US005661122A

United States Patent [19]
Clark et al.

[11] Patent Number: 5,661,122
[45] Date of Patent: Aug. 26, 1997

[54] TREATMENT OF CONGESTIVE HEART FAILURE

[75] Inventors: Ross G. Clark, Pacifica; Hongkui Jin, San Bruno; Nicholas F. Paoni, Belmont; Renhui Yang, San Bruno, all of Calif.

[73] Assignee: Genentech, Inc., South San Francisco, Calif.

[21] Appl. No.: 284,859

[22] Filed: Aug. 2, 1994

Related U.S. Application Data

[63] Continuation of Ser. No. 227,923, Apr. 15, 1994, abandoned.
[51] Int. Cl.$^6$ ............................ A61K 38/00; A61K 31/40
[52] U.S. Cl. ........................................... 514/2; 514/423
[58] Field of Search ................................ 514/2, 423

[56] References Cited

U.S. PATENT DOCUMENTS 5,370,870 12/1994 Wong ........................................ 424/85.1

FOREIGN PATENT DOCUMENTS

| WO 91/18621 | 12/1991 | WIPO | ............................ A61K 37/24 |
| WO 9207578 | 5/1992 | WIPO. | |
| WO 9211865 | 7/1992 | WIPO. | |
| WO 9222311 | 12/1992 | WIPO. | |
| WO 93/00109 | 1/1993 | WIPO | ............................ A61K 37/36 |
| WO 93/00110 | 1/1993 | WIPO | ............................ A61K 37/36 |

OTHER PUBLICATIONS

Banskota et al., "Characterization of Induction of Protooncogene c-myc and Cellular Growth in Human Vascular Smooth Muscle Cells by Insulin and IGF-I" *Diabetes* 38:123–129 (1989).

Beznak, "The Restoration of Cardiac Hypertrophy and Blood Pressure in Hypophysectomized Rats by Large Doses of Lyophilized Anterior Pituitary and Growth Hormone" *J. Physiol. (Lond.)* 124:64–74 (1954).

Boulware et al., "Diverse Effects of Insulin-like Growth Factor I on Glucose, Lipid, and Amino Acid Metabolism" *Am. J. Physiol.* 262:E130–E133 (1992).

Bugaisky et al., "Cellular and Molecular Mechanisms of Cardiac Hypertrophy" *The Heart and Cardiovascular System* 2:1621–1640 (1992).

Caidahl et al., "Cardiovascular and Renal Effects of Growth Hormone" *Acta Endocrinologica* 128 (Suppl. 2) : 68 (1993).

Chanson et al., "Cardiovascular Effects of the Somatostatin Analog Octreotide in Acromegaly" *Annals Int. Med.* 113:921–925 (1990).

Cittadini et al., "Impaired Cardiac Performance in GH-Deficient Adults and its Improvement after GH Replacement" *Am. J. Physiol.* 267:E219–E225 (1994).

Cuneo et al., "Cardiac Failure Responding to Growth Hormone" *Lancet* pp. 838–839 (1989).

Cuneo et al., "Cardiovascular effects of growth hormone treatment in growth-hormone-deficient adults: stimulation of the renin-aldosterone system" *Clinical Science* 81:587–592 (1991).

Cuneo et al., "Growth Hormone Treatment Improves Serum Lipids and Lipoproteins in Adults with Growth Hormone Deficiency" *Metabolism* 42(12) : 1519–1523 (Dec. 1993).

Donohue et al., "Evidence that Antihypertensive Agents Lessen Ventricular Hypertrophy by Inhibiting Cardiac Expression of Insulin-like Growth Factor-I" *J. Am. Coll. Cardiol.* 19:85A (Mar. 1992).

Donohue et al., "Induction of Myocardial Insulin-like Growth Factor-I Gene Expression in Left Ventricular Hypertrophy" *Circulation* 89(2):799–809 (1994).

Flyvbjerg et al., "Inhibitory Effect of Octreotide on Growth Hormone-Induced IGF-I Generation and Organ Growth in Hypophysectomized Rats" *Am. J. Physiol.* 260:E568–E574 (1991).

Friberg et al., "Right but not Left Ventricular Insuline-Like Growth Factor 1 (IGF-1) and Growth Hormone (GH)-Receptor Levels Increase After Induction of Volume Overload" *Hypertension* 22(3):418 (A65) (Sep. 1993).

Frustaci et al., "Reversible Dilated Cardiomyopathy Due to Growth Hormone Deficiency" *Am. J. Clin. Pathol.* 97:503–511 (1992).

Gilbert et al., "Cardiac Morphology in Rats with Growth Hormone-producing Tumours" *J. Mol Cell Cardiol* 17:805–811 (1985).

Guler et al., "Recombinant human insulin-like growth factor I stimulates growth and has distinct effects on organ size in hypophysectomized rats" *Proc. Natl. Acad. Sci. USA* 85:4889–4893 (1988).

Guse et al., "Identification and Characterization of Insulin-like Growth Factor Receptors on Adult Rat Cardiac Myocytes: Linkage to Inositol 1,4,5-Trisphosphate Formation" *Endocrinology* 130(1):145–151 (1992).

Hanson et al., "Induction of Cardiac Insulin-Like Growth Factor I Gene Expression in Pressure Overload Hypertrophy" *Am. J. Med. Sci.* 306:69–74 (1993).

Hayward et al., "Acromegalic Heart Disease: Influence of Treatment of the Acromegaly on the Heart" *Qtr J of Med.* 62(237):41–58 (1987).

(List continued on next page.)

*Primary Examiner*—Kimberly Jordan
*Attorney, Agent, or Firm*—Janet E. Hasak; Walter H. Dreger

[57] ABSTRACT

Methods of enhancing myocardial contractility and cardiac performance in a mammal with congestive heart failure are disclosed. In a first method a mammal with congestive heart failure is treated by administering to the mammal an effective amount of a combination of growth hormone (GH) and insulin-like growth factor (IGF-I). A second method comprises administering to the mammal an effective amount of a combination of GH and IGF-I in the presence of an ACE inhibitor. This method results in enhancement of myocardial contractility and cardiac performance above the level achieved with ACE inhibition alone. Preferably the mammal is a human.

8 Claims, 6 Drawing Sheets

Hirsch et al., "Cardiac Function in Acromegaly" *Am. J. Med. Sciences* 257:1–8 (1969).

Hjalmarson et al., "Effects of Growth Hormone and Insulin on Amino Acid Transport in Perfused Rat Heart" *Am. J. Physiol.* 217(6): 1795–1802 (1969).

Isgaard et al., "Growth Hormone Regulates the Level of Insulin–like Growth Factor–I mRNA in Rat Skeletal Muscle" *J. Endocrinol.* 120:107–112 (1989).

Ito et al., "Insulinlike Growth Factor–I Induces Hypertrophy With Enhanced Expression of Muscle Specific Genes in Cultured Rat Cardiomyocytes" *Circulation* 87:1715–1721 (1993).

Jorgensen et al., "Long–term Growth Hormone Treatment in Growth Hormone Deficient Adults" *Acta Endocrinologica* 125:449–453 (1991).

Kahaly et al., "Relation of endocrine and cardiac findings in acromegalics" *J Endocrinol Invest.* 15:13–18 (1992).

Korner, "Anabolic Action of Growth Hormone" *Ann. N.Y. Acad. Sci.* 148:408–418 (1968).

Kostyo and Nutting, "Growth Hormone and Protein Metabolism" *Handbook of Physiology*, Greep et al., Washington, DC: American Physiological Society vol. IV, part 2 (Sect. 7):187–210 (1974).

LaFranchi et al., "Effect of Growth Hormone Replacement on Development of Hypothyroidism and Hyperlipidemia" *J. Pediatrics* 106:588–593 (1985).

Lie et al., "Pathology of the heart in acromegaly: anatomic findings in 27 autopsied patients" *Amer Heart J.* 100:41–52 (1980).

Luboshitzki et al., "The Heart in Acromegaly: Correlation of Echocardiographic and Clinical Findings" *Isr. J. Med Sci.* 16:378–383 (1980).

Martins et al., "Cardiac Size and Function in Acromegaly" *Circulation* 56:863–869 (1977).

Mather et al., "Heart size and function in acromegaly" *British Heart Journal* 41:697–701 (1979).

Mathews et al., "Regulation of Rat Growth Hormone Receptor Gene Expression" *Journal of Biological Chemistry* 264:9905–9910 (1989).

McGuffin et al., "Acromegaly and Cardiovascular Disorders" *Annals of Internal Medicine* 81:11–18 (1974).

Prysor–Jones and Jenkins, "Effect of Excessive Secretion of Growth Hormone on Tissues of the Rat, with Particular Reference to the Heart and Skeletal Muscle" *J. Endocr.* 85:75–82 (1980).

Rodrigues et al., "Subclinical cardiac dysfunction in acromegaly: evidence for a specific disease of heart muscle" *Br Heart J* 62:185–194 (1989).

Rosen and Bengtsson, "Premature Mortality Due to Cardiovascular Disease in Hypopituitarism" *Lancet* 336:285–288 (1990).

Rosen et al., "Cardiovascular Risk Factors in Adult Patients with Growth Hormone Deficiency" *Acta Endocrinologica* 129:195–200 (1993).

Savage et al., "Echocardiographic Assessment of Cardiac Anatomy and Function in Acromegalic Patients" *The Amer. J of Med.* 67:823–829 (1979).

Sklar et al., "Developmental Expression of the Tissue Insulin–like Growth Factor II/Mannose 6–Phosphate Receptor in the Rat" *Journal of Biological Chemistry* 264(28):16733–16738 (1989).

Smallridge et al., "Acromegaly and the Heart" *The Amer. J of Med.* 66:22–27 (1979).

Wahlander et al., "Left Ventricular Insulin–like Growth Factor I Increases in Early Renal Hypertension" *Hypertension* 19:25–32 (1992).

Xu and Best, "Decreased transient outward K+ current in ventricular myocytes from acromegalic rats" *Am J. Physiol* 260:H935–H942 (1991).

CA 120:208271, Takeda et al., 1993.

Amato et al., "Body Composition, Bone Metabolism, and Heart Structure and Function in Growth Hormone (GH)–Deficient Adults before and after GH Replacement Therapy at Low Doses", *J. Clin. Endocrinol Metab.*, 77:1671–76 (1993).

Ambler et al., "Improvement of doxorubicin induced cardiomyopathy in rats treated with insulin–like growth factor I", *Cardiovascular Research*, 27:1368–1373 (1993).

Buttrick et al., "Effects of chronic dobutamine on cardiac mechanics and biochemistry after myocardial infarction in rats", *Am. J. Physiol* 260:11473–11479 (1991).

Caidahl et al., "Cardiovascular and renal effects of growth hormone", *Clinical Endocrinology* 40:393–400 (1994).

The Captopril–Digoxin Multicenter Research Group, "Comparative Effects of Therapy With Captopril and Digoxin in Patients With Mild to Moderate Heart Failure", *JAMA* 259(4):539–544 (1988).

Captopril Multicenter Research Group, "A Placebo–Controlled Trial of Captopril in Refractory Chronic Congestive Heart Failure", *JACC* 2(4):755–763 (1983).

Castagnino et al., "Bivalent Effects of Human Growth Hormone in Experimental Myocardial Infarcts; Protective When Administered Alone and Aggravating When Combined with Beta Blockers", 31:845–855 (1990).

Castagnino et al., "Preservation of the myocardial collagen framework by human growth hormone in experimental infarctions and reduction in the incidence of ventricular aneurysms", *Int. J. Cardiol.* 35:101–114 (1992).

Celniker et al., "Variability in the Quantitation of Circulating Growth Hormone Using Commercial Immunoassays", *J. Endocrinology/Metabolism* 68:469–476 (1989).

Christiansen et al., "Beneficial effects of GH replacement therapy in adults", *Acta Endocrinol.* 125:7–13 (1991).

Christiansen et al., "Cardiovascular effects of growth hormone –with special reference to growth hormone replacement therapy", *Acta Paediatr Suppl.* 383:40–42 (1992).

Clemmons et al., "Reversal of Diet–Induced Catabolism by Infusion of Recombinant Insulin–Like Growth Factor–I in Humans", *J. Clin Endocrinol* 75:234–238 (1992).

Cohn et al., "A Comparison Of Enalapril With Hydralazine–Isosorbide Dinitrate In The Treatment Of Chronic Congestive Heart Failure", *The New England Journal of Medicine*, 325(5):303–310 (1991).

The Consensus Trial Study Group, "Effects Of Enalapril On Mortality In Severe Congestive Heart Failure", *The New England Journal of Medicine* 316(23):1429–1435 (1987).

Csanady et al., "The heart in acromegaly: an echocardiographic study", *Int. J. Cardiol* 2:349–361 (1983).

Cuneo et al., "Growth hormone treatment in growth hormone–deficient adults. II. Effects on exercise performance", *J. Appl. Physiol* 70:695–700 (1991).

Fazio et al., "Evidence for biventricular involvement in acromegaly: a Doppler echocardiographic study", *Eur Heart J.* 14:26–33 (1993).

Florini, "Hormonal Control of Muscle Growth", *Muscle & Nerve* 10:577–598 (1987).

Froesch et al., "Therapeutic Potential of Insulinlike Growth Factor I", *Trends in Endocrinology/Metabolism* 1(5):254–260 (1990).

Furlanetto et al., "Estimation of Somatomedin-C Levels in Normals and Patients with Pituitary Disease by Radioimmunoassay", *The Journal of Clinical Investigation* 60:648–657 (1977).

Geenen et al., "Papillary mechanics and cardiac morphology of infarcted rat hearts after training", *J. Appl. Physical*, 63:92–96 (1987).

Guler et al., "Short-Term Metabolic Effects Of Recombinant Human Insulin–Like Growth Factor I In Healthy Adults", *The New England Journal of Medicine* 317(3):137–140 (1987).

Jorgensen et al., "Beneficial Effects of Growth Hormone Treatment in GH-Deficient Adults", *The Lancet* pp. 1221–1225 (1989).

Kahaly et al., "Arrhythmia profile in acromegaly", *Eur Heart J.* 13:51–56 (1992).

Kloner et al., "The effect of early exercise on myocardial infarct scar formation", *Amer. Heart Journal* 106(5):1009–1013 (1983).

Kramer et al., "Controlled Trial in Chronic Heart Failure: A Rest and Exercise Hemodynamic Study", *Circulation* 67(4):807–816 (1983).

Kupfer et al., "Enhancement of the Anabolic Effects of Growth Hormone and Insulin–Like Growth Factor I by Use of Both Agents Simultaneously", *Amer. Soc. for Clin. Invest.* 91:391–396 (1993).

Lei et al., "Cardiac Architectural Changes with Hypertrophy Induced by Excess Growth Hormone in Rats", *Lab Invest.*, 59:357–362 (1988).

Lim et al., "Rapid Reduction of Left Ventricular Hypertrophy in Acromegaly after Suppression of Growth Hormone Hypersecretion", *Ann Intern Med.*, 117:719–726 (1992).

Mayoux et al., "Mechanical Properties of Rat Cardiac Skinned Fibers Are Altered by Chronic Growth Hormone Hypersecretion", *Circulation Research* 72(1):57–64 (1993).

Merola et al., "Cardiac Structural and Functional Abnormalities in Adult Patients with Growth Hormone Deficiency", *J. Clin. Endocrinol Metab* 77:1658–1661 (1993).

Metcalfe et al., "Metabolic Effects of Acute and Prolonged Growth Hormone Excess in Normal and Insulin–deficient Man", *Diabetologia* 20:123–128 (1981).

Penney et al., "Cardiomegaly and haemodynamics in rats with a transplantable growth hormone–secreting tumour", *Cardiovascular Research* 19:270–277 (1985).

Pollock et al., "Usefulness of Bucindolol in Congestive Heart Failure", *Am J Cardiol* 66:603–607 (1990).

Rubin et al., "Cardiac Physiology, Biochemistry and Morphyology in Response to Excess Growth Hormone in the Rat", *Mol. Cell Cardiol* 22:429–438 (1990).

Shahi et al., "Myocardial dysfunction in treated adult hypopituitarism: a possible explanation for increased cardiovascular mortality", *Br Heart J* 67:92–96 (1992).

Sherwin et al., "Effect of Growth Hormone on Oral Glucose Tolerance and Circulating Metabolic Fuels in Man", *Diabetologia* 24:155–161 (1983).

Sicolo et al., "Acromegalic cardiopathy: A left ventricular scintigraphic study", *J. Endocrinol. Invest.* 16:123–127 (1993).

The SOLVD Investigators, "Effect Of Enalapril On Survival In Patients With Reduced Left Ventricular Ejection Fractions And Congestive Heart Failure", *The New England Journal of Medicine* 325(5) 293–302 (1991).

Takano et al., "Effects of sc Administration of Recombinant Human Insulin–Like Growth Factor (IGF–I) on Normal Human Subjects", *Endocrinol. Japon.* 37(2):309–317 (1990).

Thuesen et al., "Increased myocardial contractility following growth hormone administration in normal man", *Danish Medical Bulletin* 35(2):193–196 (1988).

Timsit et al., "Effects of chronic growth hormone excess on cardiac contractility and myosin phenotype in the rat", *Acta Paediatr Suppl.*, 383:32–34 (1992).

Timsit et al., "Effects of Chronic Growth Hormone Hypersecretion on Intrinsic Contractility, Energetics, Isomyosin Pattern, and Myosin Adenosine Triphosphatase Activity of Rat Left Ventricle", *The Amer. Soc. for Cin. Invest.* 86:507–515 (1990).

Vetter et al., "Insulin–like growth factors and insulin increase the contractility of neonatal rat cardiocytes in vitro", *Basic Res. Cardiol* 83:647–654 (1988).

Yang, "Cardiac Effects Of Growth Hormone In A Rat Model Of Congestive Heart Failure", *Clinical Research* 42(2):325A (1994).

Yang, R. et al., "J. Heart Failure", *Abstract Suppl* 1:793 (1993).

Moller et al., "Expansion of Extracellular Volume and Suppression of Atrial Natriuretic Peptide after Growth Hormone Administration in Normal Man", *J. Clin. Endocrinol. Metab.* 72, pp. 768–772. 1991.

Anand et al., "Growth Hormone in Syndromes of Chronic Congestive Heart Failure", Circulation, Supplement 1, 86(4), pp. I–668, abstract No. 2657. Oct. 1992.

Folkow et al., "Trophic Effects of Hypophyseal hormones on Resistance Vessels and the Heart in Normotensive and Renal Hypertensive Rats", Acta Physiol. Scand., 144, pp. 291–306. 1992.

Alexander et al., "Epidemiology of Acromegaly in the Newcastle Region", Clinical Endocrinology, 12, pp. 71–79. 1980.

TREATMENT OF CONGESTIVE HEART FAILURE

This application makes reference to, is a continuation of and claims the benefits available under 35 USC §120 of, application U.S. Ser. No. 08/227,923 filed on 15 Apr. 1994, now abandoned.

BACKGROUND OF THE INVENTION

1. Field of the Invention

This invention relates to the field of treating patients having congestive heart failure with growth hormone and insulin-like growth factor I in the presence or absence of an angiotensin-converting enzyme (ACE) inhibitor.

2. Description of Related Art

In vitro studies have shown that chronic hypersecretion of growth hormone (GH) by implantation of a GH-secreting tumor in rats leads to increased isometric force without affecting the unloaded shortening velocity of isolated cardiac papillary muscles, despite a marked shift of the isomyosin pattern toward the low ATPase activity V3 isoform. These results suggest that GH may induce a pattern of myocardial contraction that allows the cardiac muscle to function more economically. Timsit, J. et al., *J. Clin. Invest.* 86:507-515 (1990); Timsit, J. et al., *Acta. Paediatr. Suppl.* 383:32-34 (1992). The increase in the contractile performance was shown to be due to specific alterations in the properties of the contractile apparatus, including an increase in both maximal tension and myofibrillar sensitivity to calcium. Mayoux, E. et al., *Circulation Research* 72(1):57-64 (1993). However, hemodynamic studies in vivo in anesthetized rats subjected to chronic GH hypersecretion have yielded conflicting results, with either increased or decreased indices of cardiac performance. Penney, D. G. et al., *Cardiovascular Research* 19:270-277 (1985); Rubin, S. A. et al., *J. Mol. Cell Cardiol.* 22:429-438 (1990). The inconsistency between these two in vivo studies is probably related to effects of anesthesia on hemodynamics. Further, a clinical study has demonstrated that GH administration increases myocardial contractility and cardiac output in normal man. Thuesen, L. et al., *Dan. Med. Bull.* 35(2):193-196 (1988). Treatment with GH causes a significant increase in cardiac performance and improvement of exercise capacity in GH deficient adult humans. Jorgensen, J. et al., *The Lancet* i:1221-1225 (1989); Cuneo, R. et al., *J. Appl. Physiol.* 70:695-700 (1991); Christiansen, J. S. et al., *Acta. Paediatr. Suppl.* 383:40-42 (1992); Amato, G. et al., *J. Clin. Endocrinol. Metab.* 77:1671-1676 (1994); Caidahl, K. et al., *Clin. Endocrinol.* 40:393-400 (1994). Previous studies have shown that GH treatment for two weeks improved cardiac function by increasing ventricular contractility and by decreasing peripheral vascular resistance in conscious rats with congestive heart failure. Yang, R. et al., *Clinical Research* 42(2):325A (1994).

Insulin-like growth factor (IGF-I) has been shown to promote actin synthesis in myocytes in culture (Florini, J. R., *Muscle and Nerve* 10:577-598 [1987]) and to increase the contractility of neonatal rat cardiocytes in vitro. Vetter, U. et at., *Basic Res. Cardiol.* 83:647-654 (1988). Acute intravenous administration (infusion or bolus injection) of IGF-I produces increases in stroke volume and cardiac output in normal lambs. Gluckman et al., PCT WO 92/11865 (1992). In rats with doxorubicin induced cardiomyopathy, chronic treatment with IGF-I for 3 weeks increases cardiac output and stroke volume. Ambler, G. R. et al., *Cardiovascular Research* 27:1368-1373 (1993).

The effect of GH on circulating levels of glucose is opposite that of IGF-I. GH administration can cause glucose intolerance or increase blood sugar levels, producing hyperglycemia in humans. Sherwin, R. S. et al., *Diabetologia* 24:155-156 (1983); Metcalfe, P. et al., *Diabetologia* 20:123-128 (1981). In contrast, subcutaneous or intravenous administration of IGF-I can lower blood glucose, inducing hypoglycemia in humans. Guler, H. P. et al., *N. Engl. J. Med.* 317:137-140 (1987); Takano, K. et al., *Endocrinol. Japan.* 37(2):309-317 (1990); Froesch, E. R. et al., *Trends Endocrinol. Metab.* 1:254-260 (1990). Further, a clinical study has demonstrated that the combination of GH and IGF-I treatment is substantially more anabolic than either GH or IGF-I alone. The combination also prevents the hyperglycemia caused by GH alone and attenuates the hypoglycemia induced by IGF-I alone in normal subjects. Kupfer, S. R. et al., *J. Clin. Invest.* 91:391-396 (1993); Clemmons, D. R. et al., *J. Clin. Endocrinol. Metab.* 75:234-238 (1992).

Heart failure affects approximately three million Americans. New cases of heart failure number about 400,000 each year. Congestive heart failure is a syndrome characterized by left ventricular dysfunction, reduced exercise tolerance, impaired quality of life, and markedly shortened life expectancy. Decreased contractility of the left ventricle leads to reduced cardiac output with consequent systemic arterial and venous vasoconstriction. This vasoconstriction, which promotes the vicious cycle of further reductions of stroke volume followed by an increased elevation of vascular resistance, appears to be mediated, in part, by the renin-angiotensis system. The key component of this system, the potent vasoconstrictor, angiotensin II, also has the effect of stimulating aldosterone secretion, possibly enhancing sympathetic drive and increasing vasopressin secretion. Cohn, J. N. et al., *N. England J. Med.* 325(5):303-310 (1991); Captopril Multicenter Research Group, *J. A. C. C.* 2(4):755-763 (1983). Angiotensin-converting enzyme (ACE) inhibitors, such as captopril, have become standard therapy for patients with congestive heart failure. These drugs improve hemodynamic profile and exercise tolerance and reduce the incidence of morbidity and mortality in patients with congestive heart failure. Kramer, B. L. et al., *Circulation* 67(4):807-816 (1983); Captopril Multicenter Research Group, *J. A. C. C.* 2(4):755-763 (1983); The CONSENSUS Trial Study Group, *N. Engl. J. Med.* 316(23):1429-1435 (1987); The SOLVD Investigators, *N. Engl. J. Med.* 325(5):293-302 (1991). However, despite proven efficacy, response to ACE inhibitors has been limited. Improvement of functional capacity and exercise time is only small and mortality, although reduced, continues to be high. The CONSENSUS Trial Study Group, *N. Engl. J. Med.* 316(23):1429-1453 (1987); The SOLVD Investigators, *N. Engl. J. Med.* 325(5):293-302 (1991); Cohn, J. N. et al., *N. Engl. J. Med.* 325(5):303-310 (1991); The Captopril-Digoxin Multicenter Research Group, *JAMA* 259(4):539-544 (1988). GH and IGF-I have each been shown separately to improve cardiac performance. However, until now the effects of the combination of GH and IGF-I in heart failure have not been evaluated, either in the presence or absence of captopril.

Accordingly, it is an object of this invention to provide a method of treatment for patients with congestive heart failure, the method comprising administering to the patient GH and IGF-I in addition to an ACE inhibitor. It is well known, that captopril alone, for example, improves cardiac function by decreasing peripheral vascular resistance. Captopril together with GH and IGF-I cause greater improvement of cardiac performance than does captopril alone.

It is another object of this invention to provide a method of treatment for patients with congestive heart failure, the method comprising treating the patients with an effective amount of a combination of GH and IGF-I in the absence of an ACE inhibitor. The administration of GH and IGF-I in combination produces improvement of cardiac performance by increased ventricular contractility and decreased peripheral vascular resistance.

Improvement in cardiac performance for patients with congestive heart failure may be achieved in patients being treated with ACE inhibitors by adding to the treatment regimen a combination of GH and IGF-I. Improvement in cardiac performance in these patients may also be achieved by administration of GH/IGF-I and an ACE inhibitor from the outset of treatment.

SUMMARY OF THE INVENTION

The present invention achieves these objects by providing a method of treatment of congestive heart failure, the method characterized by administration of an effective amount of GH and IGF-I (GH/IGF-I) with or without an ACE inhibitor.

In one aspect, the present invention provides a method of treating a mammal exhibiting congestive heart failure comprising administering to the mammal an effective amount of a combination of GH and IGF-I and an ACE inhibitor. Administration of GH and IGF-I may be started after a period of treatment with the ACE inhibitor.

In another aspect, the invention provides a method of treating a mammal exhibiting congestive heart failure comprising administering to said mammal an effective amount of a combination of GH and IGF-I in the absence of an ACE inhibitor.

Figure 1A:
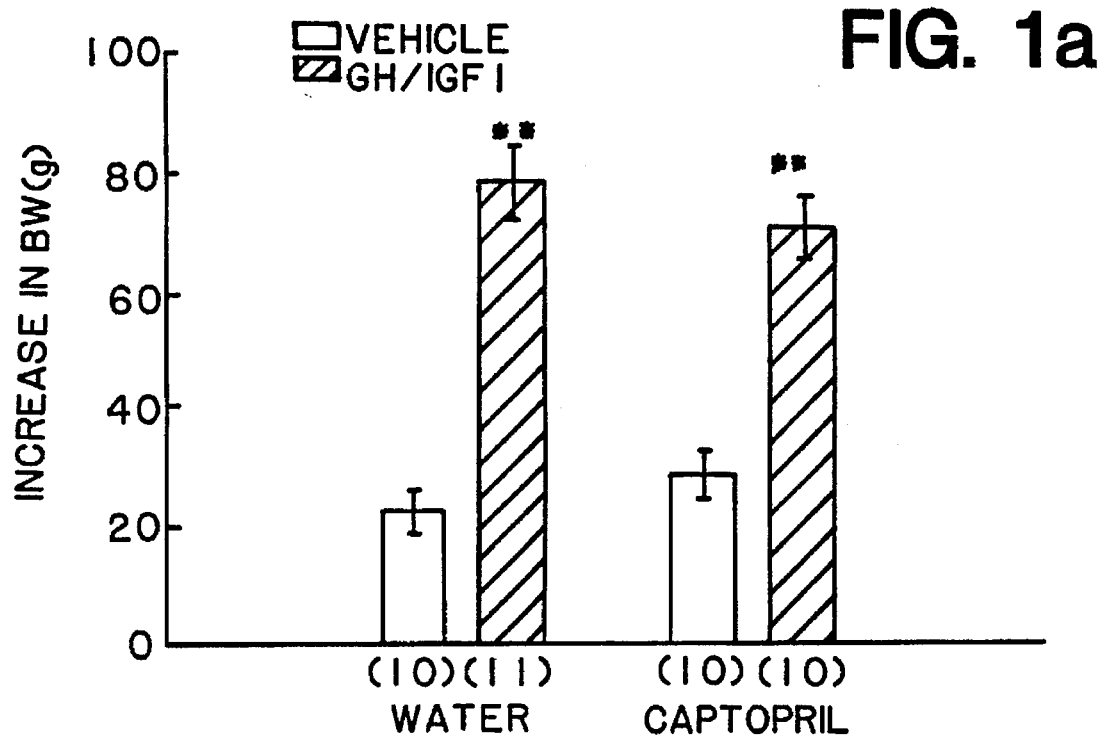
FIG. 1a shows the effect of growth hormone and insulin-like growth factor (GH/IGF-I) (hatched bars) and carrier vehicle for GH/IGF-I alone (open bars) on body weight (BW) in water-treated and captopril-treated rats. **$P<0.01$, compared to the respective vehicle group.

DETAILED DESCRIPTION OF THE INVENTION a. Definitions

In general, the following words or phrases or abbreviations have the indicated definition when used in the description, examples, and claims:

As used herein, "BW" refers to body weight.

As used herein, "CO" refers to cardiac output.

As used herein, "CI" refers to cardiac index. The cardiac index is measurable as cardiac output divided by body weight (CO/BW).

As used herein, "HR" refers to heart rate.

As used herein, "LVEDP" refers to left ventricular end-diastolic pressure.

As used herein, "LVW" refers to left ventricular weight.

As used herein, "MAP" refers to mean arterial pressure.

As used herein, "SAP" refers to systolic arterial pressure.

As used herein, "SV" refers to stroke volume. The stroke volume is measurable as CO/HR.

As used herein, "SVI" refers to stroke volume index. The stroke volume index is measurable as SV/BW.

As used herein, "SVR" refers to systemic vascular resistance. The SVR is measurable as MAP/CI.

As used herein "congestive heart failure" refers to a syndrome characterized by left ventricular dysfunction, reduced exercise tolerance, impaired quality of life, and markedly shortened life expectancy. Decreased contractility of the left ventricle leads to reduced cardiac output with consequent systemic arterial and venous vasoconstriction. This vasoconstriction, which appears to be mediated, in part, by the renin-angiotensis system, promotes the vicious cycle of further reductions of stroke volume followed by an increased elevation of vascular resistance.

As used herein "treatment" refers to induction of increased myocardial contractility and cardiac performance in patients experiencing congestive heart failure, as well as to prevention of congestive heart failure. Where the combination of GH and IGF-I is used in conjunction with an ACE inhibitor, the level of increased myocardial contractility and cardiac performance is increased above that resulting from use of the ACE inhibitor alone.

As used herein "infarct" refers to an area of necrosis resulting from an insufficiency of blood supply. "Myocardial infarction" refers to myocardial necrosis resulting from the insufficiency of coronary blood supply.

As used herein, the term "mammal" refers to any animal classified as a mammal, including humans, domestic and farm animals, and zoo, sports, or pet animals such as dogs, horses, cats, cows, etc. Preferably, the mammal herein is human.

As used herein, "ACE inhibitor" refers to angiotensin-converting enzyme inhibiting drugs which prevent the conversion of angiotensin I to angiotensin II. The ACE inhibitors may be beneficial in congestive heart failure by reducing systemic vascular resistance and relieving circulatory congestion. The ACE inhibitors include but are not limited to those designated by the trademarks Accupril® (quinapril), Altace® (ramipril), Capoten® (captopril), Lotensin® (benazepril), Monopril® (fosinopril), Prinivil® (lisinopril), Vasotec® (enalapril), and Zestril® (lisinopril). One example of an ACE inhibitor is that sold under the trademark Capoten®. Generically referred to as captopril, this ACE inhibitor is designated chemically as 1-[(2S)-3-mercapto-2-methylpropionyl]-L-proline.

As used herein, "growth hormone" or "GH" refers to growth hormone in native-sequence or in variant form, and from any source, whether natural, synthetic, or recombinant. Examples include human growth hormone (hGH), which is natural or recombinant GH with the human native sequence (somatotropin or somatropin), and recombinant growth hormone (rGH), which refers to any GH or variant produced by means of recombinant DNA technology, including somatrem, somatotropin, and somatropin. Preferred herein for human use is recombinant human native-sequence, mature GH with or without a methionine at its N-terminus. More preferred is methionyl human growth hormone (met-hGH) produced in *Escherichia coli*, e.g., by the process described in U.S. Pat. No. 4,755,465 issued Jul. 5, 1988 and Goeddel et al., *Nature* 282:544 (1979). Met-hGH, which is sold under the trademark Protropin® by Genentech, Inc., is identical to the natural polypeptide, with the exception of the presence of an N-terminal methionine residue. This added amino acid is a result of the bacterial protein synthesis process. Also preferred is recombinant hGH available from Genentech, Inc. under the trademark Nutropin®. This latter hGH lacks this methionine residue and has an amino acid sequence identical to that of the natural hormone. See Gray et al., *Biotechnology* 2:161 (1984). Both methionyl hGH and hGH have equivalent potencies and pharmacokinetic values. Moore et al., *Endocrinology* 122:2920–2926 (1988). Another appropriate hGH candidate is an hGH variant that is a placental form of GH with pure somatogenic and no lactogenic activity as described in U.S. Pat. No. 4,670,393 issued 2 Jun., 1987. Also included are GH variants as described in WO 90/04788 published 3 May, 1990 and WO 92/09690 published 11 Jun., 1992.

As used herein, "IGF-I" refers to insulin-like growth factor from any species, including bovine, ovine, porcine, equine, avian, and preferably human, in native-sequence or in variant form, and from any source, whether natural, synthetic, or recombinant. IGF-I has been isolated from human serum and produced recombinantly. See, e.g., EP 123,228 and 128,733.

Preferred herein for animal use is that form of IGF-I from the particular species being treated, such as porcine IGF-I to treat pigs, ovine IGF-I to treat sheep, bovine IGF-I to treat cattle, etc. Preferred herein for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations.

The preferred IGF-I variants are those described in U.S. Pat. No. 5,077,276 issued Dec. 31, 1991, in PCT WO 87/01038 published Feb. 26, 1987 and in PCT WO 89/05822 published Jun. 29, 1989, i.e., those wherein, at least, the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-I, des(1–3)-IGF-I, or des-IGF-I).

b. Modes for Carrying Out The Invention

The GH, in combination with IGF-I, is directly administered to the mammal by any suitable technique, including parenterally, intranasally, orally, or by absorption through the skin. They need not be administered by the same route and can be administered locally or systemically. The specific route of administration of each agent will depend, e.g., on the medical history of the patient, including any perceived or anticipated side or reduced anabolic effects using hGH or IGF-I alone. Examples of parenteral administration include subcutaneous, intramuscular, intravenous, intraarterial, and intraperitoneal administration. Subcutaneous and intravenous injection or infusion is preferred.

The GH and IGF-I are administered so as to be in effective amounts. The GH may be administered non-continuously, such as at particular times (e.g., once daily) in the form of an injection of a particular dose, where there will be a rise in plasma GH concentration at the time of the injection, and then a drop in plasma GH concentration until the time of the next injection. Another non-continuous administration method results from the use of many implant devices available that provide a discontinuous release of active ingredient, such as an initial burst, and then a lag before release of the active ingredient. See, e.g., U.S. Pat. No. 4,767,628, col. 2, lines 19–37.

However, more preferably the GH is administered so as to have a continual presence in the blood that is maintained for the duration of the administration of the GH. This is most preferably accomplished by means of continuous infusion via, e.g., mini-pump such as osmotic mini-pump. Alternatively, it is properly accomplished by use of frequent injections of GH (i.e., more than once daily, for example, twice or three times daily).

For administration, GH may be complexed or bound to a polymer to increase its circulatory half-life. Examples of polyethylene polyols and polyoxyethylene polyols useful for this purpose include polyoxyethylene glycerol, polyethylene glycol, polyoxyethylene sorbitol, polyoxyethylene glucose, or the like. The glycerol backbone of polyoxyethylene glycerol is the same backbone occurring in, for example, animals and humans in mono-, di-, and triglycerides.

The polymer need not have any particular molecular weight, but it is preferred that the molecular weight be between about 3500 and 100,000, more preferably between 5000 and 40,000. Preferably the PEG homopolymer is unsubstituted, but it may also be substituted at one end with an alkyl group. Preferably, the alkyl group is a C1–C4 alkyl group, and most preferably a methyl group. Most preferably, the polymer is an unsubstituted homopolymer of PEG, a monomethyl-substituted homopolymer of PEG (mPEG), or polyoxyethylene glycerol (POG) and has a molecular weight of about 5000 to 40,000.

The GH is covalently bonded via one or more of the amino acid residues of the GH to a terminal reactive group on the polymer, depending mainly on the reaction conditions, the molecular weight of the polymer, etc. The polymer with the reactive group(s) is designated herein as activated polymer. The reactive group selectively reacts with free amino or other reactive groups on the GH. It will be understood, however, that the type and amount of the reactive group chosen, as well as the type of polymer employed, to obtain optimum results, will depend on the particular GH employed to avoid having the reactive group react with too many particularly active groups on the GH. As this may not be possible to avoid completely, it is recommended that generally from about 0.1 to 1000 moles, preferably 2 to 200 moles, of activated polymer per mole of protein, depending on protein concentration, is employed. The final amount of activated polymer per mole of protein is a balance to maintain optimum activity, while at the same time optimizing, if possible, the circulatory half-life of the protein.

While the residues may be any reactive amino acids on the protein, such as one or two cysteines or the N-terminal amino acid group, preferably the reactive amino acid is lysine, which is linked to the reactive group of the activated polymer through its free epsilon-amino group, or glutamic or aspartic acid, which is linked to the polymer through an amide bond.

The covalent modification reaction may take place by any appropriate method generally used for reacting biologically active materials with inert polymers, preferably at about pH 5–9, more preferably 7–9 if the reactive groups on the GH are lysine groups. Generally, the process involves preparing an activated polymer (with at least one terminal hydroxyl group), preparing an active substrate from this polymer, and thereafter reacting the GH with the active substrate to produce the GH suitable for formulation. The above modification reaction can be performed by several methods, which may involve one or more steps. Examples of modifying agents that can be used to produce the activated polymer in a one-step reaction include cyanuric acid chloride (2, 4, 6-trichloro-S-triazine) and cyanuric acid fluoride.

In one embodiment the modification reaction takes place in two steps wherein the polymer is reacted first with an acid anhydride such as succinic or glutaric anhydride to form a carboxylic acid, and the carboxylic acid is then reacted with a compound capable of reacting with the carboxylic acid to form an activated polymer with a reactive ester group that is capable of reacting with the GH. Examples of such compounds include N-hydroxysuccinimide, 4-hydroxy-3-nitrobenzene sulfonic acid, and the like, and preferably N-hydroxysuccinimide or 4-hydroxy-3-nitrobenzene sulfonic acid is used. For example, monomethyl substituted PEG may be reacted at elevated temperatures, preferably about 100°–110° C. for four hours, with glutaric anhydride. The monomethyl PEG-glutaric acid thus produced is then reacted with N-hydroxysuccinimide in the presence of a carbodiimide reagent such as dicyclohexyl or isopropyl carbodiimide to produce the activated polymer, methoxypolyethylene glycolyl-N-succinimidyl glutarate, which can then be reacted with the GH. This method is described in detail in Abuchowski et al., *Cancer Biochem. Biophys.* 7:175–186 (1984). In another example, the monomethyl substituted PEG may be reacted with glutaric anhydride followed by reaction with 4-hydroxy-3-nitrobenzene sulfonic acid (HNSA) in the presence of dicyclohexyl carbodiimide to produce the activated polymer. HNSA is described by Bhatnagar et al., Peptides: Synthesis-Structure-Function, *Proceedings of the Seventh American Peptide Symposium*, Rich et al. (eds.) (Pierce Chemical Co., Rockford Ill., 1981), p. 97–100, and in Nitecki et al., *High-Technology Route to Virus Vaccines* (American Society for Microbiology:Washington, D.C. 1986) entitled "Novel Agent for Coupling Synthetic Peptides to Carriers and Its Applications."

Specific methods of producing GH conjugated to PEG include the methods described in U.S. Pat. No. 4,179,337 on PEG-GH and U.S. Pat. No. 4,935,465, which discloses PEG reversibly but covalently linked to GH. Other specific methods for producing PEG-GH include the following:

PEGylation with methoxypolyethylene glycol aldehyde (Me-PEG aldehyde) by reductive alkylation and purification is accomplished by adding to 2 mg/mL of GH in PBS pH 7.0, 5 mM of Me-PEG aldehyde-5000 (molecular weight 5000 daltons) and 20 mM of $NaCNBH_3$ and gently mixing at room temperature for 3 hours. Ethanolamine is then added to 50 mM to reductively amidate the remaining unreacted Me-PEG. The mixture is separated on an anion-exchange column, FPLC Mono Q. The surplus unreacted Me-PEG does not bind to the column and can then be separated from the mixture. Two main PEGylated GH fractions are obtained with apparent molecular weights of 30K and 40K on reduced SDS-PAGE, vs. 20K of the unreacted GH. GH-GHBP complex is PEGylated in the same manner to give a derivative of 150K by gel filtration.

PEGylation with N-hydroxysuccinimidyl PEG (NHS-PEG) and purification are accomplished by adding NHS-PEG at a 5-fold molar excess of the total lysine concentration of GH to a solution containing 2 mg/mL of GH in 50 mM of sodium borate buffer at pH 8.5 or PBS at pH 7, and mixing at room temperature for one hour. Products are separated on a Superose 12 sizing column and/or Mono Q of FPLC. The PEGylated GH varies in size depending on the pH of the reaction from approximately 300K for the reaction run at pH 8.5 to 40K for pH 7.0 as measured by gel filtration. The GH-GHBP complex is also PEGylated the same way with a resulting molecular weight of 400 to 600 Kd from gel filtration.

PEGylation of the cysteine mutants of GH with PEG-maleimide is accomplished by preparing a single cysteine mutant of GH by site-directed mutagenesis, secreting it from an *E. coli* 16C9 strain (W3110 delta tonA phoA delta E15 delta (argF-lac)169 deoC2 that does not produce the deoC protein and is described in U.S. Ser. No. 07/224,520 filed 26 Jul., 1988, now abandoned, the disclosure of which is incorporated herein by reference) and purifying it on an anion-exchange column. PEG-maleimide is made by reacting monomethoxyPEG amine with sulfo-MBs in 0.1M sodium phosphate pH 7.5 for one hour at room temperature and buffer exchanged to phosphate buffer pH 6.2. Next, GH with a free extra cysteine is mixed in for one hour and the final mixture is separated on a Mono Q column as in Me-PEG aldehyde PEGylated GH.

As ester bonds are chemically and physiologically labile, it may be preferable to use a PEG reagent in the conjugating reaction that does not contain ester functionality. For example, a carbamate linkage can be made by reacting PEG-monomethyl ether with phosgene to give the PEG-chloroformate. This reagent could then be used in the same manner as the NHS ester to functionalize lysine side-chain amines. In another example, a urea linkage is made by reacting an amino-PEG-monomethyl ether with phosgene. This would produce a PEG-isocyanate that will react with lysine amines.

A preferred manner of making PEG-GH, which does not contain a cleavable ester in the PEG reagent, is described as follows: Methoxypoly (ethylene glycol) is converted to a carboxylic acid by titration with sodium naphthalene to generate the alkoxide, followed by treatment with bromoethyl acetate to form the ethyl ester, followed by hydrolysis to the corresponding carboxylic acid by treatment with sodium hydroxide and water, as reported by Bückmann et al., *Macromol. Chem.* 182:1379–1384 (1981). The resultant carboxylic acid is then converted to a PEG-N-hydroxysuccinimidyl ester suitable for acylation of GH by reaction of the resultant carboxylic acid with dicyclohexylcarbodiimide and NHS in ethyl acetate.

The resultant NHS-PEG reagent is then reacted with 12 mg/mL of GH using a 30-fold molar excess over GH in a sodium borate buffer, pH 8.5, at room temperature for one hour and applied to a Q Sepharose column in Tris buffer and eluted with a salt gradient. Then it is applied to a second column (phenyl Toyopearl) equilibrated in 0.3M sodium citrate buffer, pH 7.8. The PEGylated GH is then eluted with a reverse salt gradient, pooled, and buffer-exchanged using a G25 desalting column into a mannitol, glycine, and sodium phosphate buffer at pH 7.4 to obtain a suitable formulated PEG7-GH.

The PEGylated GH molecules and GH-GHBP complex can be characterized by SDS-PAGE, gel filtration, NMR, tryptic mapping, liquid chromatography-mass spectrophotometry, and in vitro biological assay. The extent of PEGylation is suitably first shown by SDS-PAGE and gel filtration and then analyzed by NMR, which has a specific resonance peak for the methylene hydrogens of PEG. The number of PEG groups on each molecule can be calculated from the NMR spectrum or mass spectrometry. Polyacrylamide gel electrophoresis in 10% SDS is appropriately run in 10 mM Tris-HCl pH 8.0, 100 mM NaCl as elution buffer. To demonstrate which residue is PEGylated, tryptic mapping can be performed. Thus, PEGylated GH is digested with trypsin at the protein/enzyme ratio of 100 to 1 in mg basis at 37° C. for 4 hours in 100 mM sodium acetate, 10 mM Tris-HCl, 1 mM calcium chloride, pH 8.3, and acidified to pH<4 to stop digestion before separating on HPLC Nucleosil C-18 (4.6 mm×150 mm, 5μ, 100A). The chromatogram is compared to that of non-PEGylated starting material. Each peak can then be analyzed by mass spectrometry to verify the size of the fragment in the peak. The fragment(s) that carried PEG groups are usually not retained on the HPLC column after injection and disappear from the chromatograph. Such disappearance from the chromatograph is an indication of PEGylation on that particular fragment that should contain at least one lysine residue. PEGylated GH may then be assayed for its ability to bind to the GHBP by conventional methods.

The various PEGylation methods used produced various kinds of PEGylated wild-type GH, with apparent molecular weights of 35K, 51K, 250K, and 300K by size exclusion chromatography, which should be close to their native hydrodynamic volume. These were designated PEG1-GH, PEG2-GH, PEG3-GH, and PEG7-GH, respectively. From the results of the tryptic mapping, the PEG1-GH and PEG2-GH both had the N-terminal 9-amino-acid fragment missing from the chromatogram and possibly PEGylated, which could be confirmed by the mass spectrometry of the big molecular species found in the flow-through of the liquid chromatograph. From the molecular weight on SDS-PAGE, PEG1-GH may have one PEG on the N-terminal amine, and the PEG2-GH may have two PEG molecules on the N-terminal amine, forming a tertiary amide. The PEG3-GH has about 5 PEG groups per molecule based upon the NMR result, and on the tryptic map, at least five peptide fragments were missing, suggesting that they are PEGylated. The PEG7-GH molecule is believed to have 6–7 PEG groups per molecule based on mass spectrometry.

The sites for adding PEG groups to GH, and those that are preferred residues for such conjugation, are N-terminal methionine or phenylalanine, lysine 38, lysine 41, lysine 70, lysine 140, lysine 145, lysine 158, and lysine 168. Two lysines that appeared not to be PEGylated were lysine 115 and lysine 172.

The GH is also suitably administered by sustained-release systems. Examples of sustained-release compositions useful herein include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman et al., *Biopolymers* 22:547–556 [1983]), poly(2-hydroxyethyl methacrylate) (Langer et al., *J. Biomed. Mater. Res.* 15:167–277 [1981], and Langer, *Chem. Tech.* 12:98–105 [1982]), ethylene vinyl acetate (Langer et al., *J. Biomed. Mater. Res.* 15:167–277 [1981]) or poly-D-(–)-3-hydroxybutyric acid (EP 133,988), or PLGA microspheres. Sustained-release GH compositions also include liposomally entrapped GH. Liposomes containing GH are prepared by methods known per se: DE 3,218,121; Epstein et al., *Proc. Natl. Acad. Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal therapy. In addition, a biologically active sustained-release formulation can be made from an adduct of the GH covalently bonded to an activated polysaccharide as described in U.S. Pat. No. 4,857,505 issued Aug. 15, 1989. In addition, U.S. Pat. No. 4,837,381 describes a microsphere composition of fat or wax or a mixture thereof and GH for slow release.

The IGF-I may be administered by any means, including injections (single or multiple, e.g., 1–4 per day) or infusions. As with the GH, the IGF-I may be formulated so as to have a continual presence in the blood during the course of treatment, as described above for GH. Thus, it may be covalently attached to a polymer or made into a sustained-release formulation as described above.

In addition, the IGF-I is appropriately administered together with any one or more of its binding proteins, for example, those currently known, i.e., IGFBP-1, IGFBP-2, IGFBP-3, IGFBP-4, IGFBP-5, or IGFBP-6. The IGF-I may also be coupled to a receptor or antibody or antibody fragment for administration. The preferred binding protein for IGF-I herein is IGFBP-3, which is described in U.S. Pat. No. 5,258,287 issued 2 Nov., 1993 and in Martin and Baxter, *J. Biol. Chem.*, 261:8754–8760 (1986). This glycosylated IGFBP-3 protein is an acid-stable component of about 53 Kd on a non-reducing SDS-PAGE gel of a 125–150 Kd glycoprotein complex found in human plasma that carries most of the endogenous IGFs and is also regulated by GH.

The administration of the IGF binding protein with IGF-I may be accomplished by the method described in U.S. Pat. No. 5,187,151, issued Feb. 16, 1993. Briefly, the IGF-I and IGFBP are administered in effective amounts by subcutaneous bolus injection in a molar ratio of from about 0.5:1 to about 3:1, preferably about 1:1.

Preferably, the administration of both IGF-I and GH is by continuous infusion using, e.g., intravenous or subcutaneous means. More preferably, the administration is subcutaneous for both IGF-I and GH.

In the treatment of congestive heart failure by GH and IGF-I in combination, the GH and IGF-I compositions will be formulated, dosed, and administered in a fashion consistent with good medical practice. Factors for consideration in this context include the particular mammal being treated, the clinical condition of the individual patient (especially the side effects of treatment with GH or IGF-I alone), the site of delivery of the IGF-I and GH composition(s), the method of administration, the scheduling of administration, and other factors known to practitioners. The "effective amounts" of each component for purposes herein are thus determined by such considerations and are amounts that improve cardiac performance or ameliorate other conditions of similar importance in congestive heart failure patients.

As a general proposition, the total pharmaceutically effective amount of each of the IGF-I and GH administered parenterally per dose will be in the range of about 1 µg/kg/day to 10 mg/kg/day of patient body weight, although, as noted above, this will be subject to a great deal of therapeutic discretion. The presence of side effects will influence the doses, as will the type of treatment (i.e., whether the treatment is chronic or acute) and the age of the patient (i.e., whether given to elderly, middle-aged, or young adults or to children). Examples of patients suited for acute treatment include burn patients, who may be treated for about 2–4 weeks. Examples of patients suited for chronic treatment include the elderly, who typically receive less drug than younger patients. Four months would be a semi-chronic dose. The dose for acute treatment is typically in a wider range and has a higher upper limit than the dose for chronic treatment.

As a general rule, the preferred dose of each of IGF-I and GH is at least about 0.01 mg/kg/day, and more preferably for humans between about 0.01 and 1 mg/kg/day for each hormone. Even more preferably, the dose of each hormone is about 0.01 mg/kg/day to 0.25 mg/kg/day. For GH specifically, the most preferred dose is given once daily in the range of about 10–100 µg/kg/day, which dose may be ramped up from an initial lower dose. Too high an initial dose of GH may cause edema. For IGF-I specifically, the most preferred dose is given twice daily (BID) in the range of about 50–200 µg/kg/day (total daily dose), preferably about 50–150 µg/kg/day. If given continuously, the IGF-I and GH are each typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The key factor in selecting an appropriate dose is the result obtained, as measured by, e.g., improved cardiac performance, relief of symptoms, exercise tolerance increase, and/or prolonged survival.

It is noted that practitioners devising doses of both IGF-I and GH should take into account the known side effects of treatment with these hormones. For hGH the side effects include sodium retention and expansion of extracellular volume (Ikkos et al., *Acta Endocrinol.* 32:341–361 (1959); Biglieri et al., *J. Clin. Endocrinol. Metab.* 21:361–370 (1961)), as well as hyperinsulinemia and hyperglycemia. The major apparent side effect of IGF-I is hypoglycemia. Guler et al., *Proc. Natl. Acad. Sci.* USA 86:2868–2872 (1989). Indeed, the combination of IGF-I and GH may lead to a reduction in the unwanted side effects of both agents (e.g., hypoglycemia for IGF-I and hyperinsulinism for GH) and to a restoration of blood levels of GH the secretion of which is suppressed by IGF-I.

For parenteral administration, in one embodiment, the IGF-I and GH are formulated generally by mixing each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IGF-I and GH each uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium, and/or non-ionic surfactants such as polysorbates, poloxamers, or PEG.

The IGF-I and GH are each typically formulated individually in such vehicles at a concentration of about 0.1 mg/mL to 100 mg/mL, preferably 1–10 mg/mL, at a pH of about 4.5 to 8. Full-length IGF-I is generally stable at a pH of no more than about 6; des(1–3)-IGF-I is stable at about 3.2 to 5; hGH is stable at a higher pH of, e.g., 7.4–7.8. It will be understood that use of certain of the foregoing excipients, carriers, or stabilizers will result in the formation of IGF-I or GH salts.

In addition, the IGF-I and GH, preferably the full-length IGF-I, may be formulated together in an appropriate carrier vehicle to form a pharmaceutical composition. In one embodiment, the buffer used for formulation will depend on whether the composition will be employed immediately upon mixing or stored for later use. If employed immediately after mixing, a mixture of full-length IGF-I and GH can be formulated in mannitol, glycine, and phosphate, pH 7.4. If this mixture is to be stored, it is formulated in a buffer at a pH of about 6, such as citrate, with a surfactant that increases the solubility of the GH at this pH, such as 0.1% polysorbate 20 or poloxamer 188. The final preparation may be a stable liquid or lyophilized solid.

IGF-I and GH to be used for therapeutic administration are preferably sterile. Sterility is readily accomplished by filtration through sterile filtration membranes (e.g., 0.2 micron membranes). Therapeutic IGF-I and GH compositions generally are placed into a container having a sterile access port, for example, an intravenous solution bag or vial having a stopper pierceable by a hypodermic injection needle.

The IGF-I and GH ordinarily will be stored in unit or multi-dose containers, for example, sealed ampoules or vials, as an aqueous solution, or as a lyophilized formulation for reconstitution. As an example of a lyophilized formulation, 10-mL vials are filled with 5 mL of sterile-filtered 1% (w/v) aqueous IGF-I and GH solutions, and the resulting mixture is lyophilized. The infusion solution is prepared by reconstituting the lyophilized IGF-I and GH using bacteriostatic Water-for-Injection.

The effective amount of ACE inhibitor to be administered, if employed, will be at the physician's or veterinarian's discretion. Dosage administration and adjustment is done to achieve optimal management of congestive heart failure and ideally takes into account use of diuretics or digitalis, and conditions such as hypotension and renal impairment. The dose will additionally depend on such factors as the type of inhibitor used and the specific patient being treated. Typically the amount employed will be the same dose as that used if the ACE inhibitor were to be administered without GH and IGF-I.

Thus, for example, a test dose of enalapril is 5 mg, which is then ramped up to 10–20 mg per day, once a day, as the patient tolerates it. As another example, captopril is initially administered orally to human patients in a test dose of 6.25 mg and the dose is then escalated, as the patient tolerates it, to 25 mg twice per day (BID) or three times per day (TID) and may be titrated to 50 mg BID or TID. Tolerance level is estimated by determining whether decrease in blood pressure is accompanied by signs of hypotension. If indicated, the dose may be increased up to 100 mg BID or TID. Captopril is produced for administration as the active ingredient, in combination with hydrochlorothiazide, and as a pH stabilized core having an enteric or delayed release coating which protects captopril until it reaches the colon. Captopril is available for administration in tablet or capsule form. A discussion of the dosage, administration, indications and contraindications associated with captopril and other ACE inhibitors can be found in the *Physicians Desk Reference,* Medical Economics Data Production Co., Montvale, N.J. 2314–2320 (1994).

The invention will be more fully understood by reference to the following examples. The examples should not, however, be construed as limiting the scope of the invention. All literature and patent citations are expressly incorporated by reference.

EXAMPLE 1

Use of GH/IGF-I to Treat Congestive Heart Failure With and Without Prior and Concurrent Treatment With Captopril Introduction The goal of this study was to evaluate the cardiac effects of human GH/IGF-I in rats with congestive heart failure with and without prior and concurrent treatment with either captopril or water.

Methods

Male Sprague-Dawley (SD) rats (Charles River Breeding Laboratories, Inc., 8 weeks of age) were acclimated to the facility for at least 1 week before surgery. Rats were fed a pelleted rat chow and water *ad libitum* and housed in a light and temperature controlled room.

Coronary arterial ligation

Myocardial infarction was produced by left coronary arterial ligation as described previously. Geenen, D. L. et al., *J. Appl. Physiol.* 63:92–96 (1987); Buttrick, P. et al., *Am. J. Physiol.* 260:H473–H479 (1991). The rats were anesthetized with sodium pentobarbital (60 mg/kg, ip), intubated via tracheotomy, and ventilated by a respirator (Harvard Apparatus Model 683). After a left-sided thoracotomy, the left coronary artery was ligated approximately 2 mm from its origin with a 7–0 silk suture. All rats were handled according to the "Position of the American Heart Association on Research Animal Use" adopted Nov. 11, 1984 by the American Heart Association. After 4–6 weeks of ligation, myocardial infarction resulted in congestive heart failure in rats.

Electrocardiograms

One week after surgery, electrocardiograms were obtained under light metofane anesthesia to document the development of infarcts. The ligated rats were subgrouped according to the depth and persistence of pathological Q waves across the precardial leads. Buttrick, P. et al., *Am. J. Physiol.* 260:H473–H479 (1991); Kloner, R. A. et al., *Am. Heart J.* 106(5):1009–1013 (1983). The ECG findings provided a gross estimate of infarct size and assured that large and small infarcts were not differently distributed in the ligated rats treated with growth factors and vehicle. Body weight (BW) was measured twice a week during the treatment.

Administration of GH and IGF-I

Two weeks after surgery, rats were placed on a treatment regimen of captopril (2 g/l in drinking water) or water for three months. Three months after captopril or water treatment was begun, vehicle or a combination of recombinant human GH (Nutropin® brand from Genentech, Inc.; 2 mg/kg/day once a day, subcutaneous injection) and recombinant human IGF-I (10 mg/ml in 50 mM sodium acetate buffer, 2.5 mg/ml phenol, 5.84 mg/ml NaCl, and 9 mg/ml benzyl alcohol, pH 5.4; 2 mg/kg/day, subcutaneous infusion by osmotic pumps) was added to the treatment of the rats in each group. Treatment continued in this manner for 14 days. GH and IGF-I were administered in water (for injection) as vehicle. Body weight (BW) was measured twice a week during the treatment.

Catheterization

After 13 days of treatment with GH/IGF-I or vehicle, rats were anesthetized with pentobarbital sodium (50 mg/kg, intraperitoneal). A catheter (PE-10 fused with PE 50) filled with heparin-saline solution (50 U/mL) was implanted into the abdominal aorta through the right femoral artery for measurement of arterial pressure and heart rate. For measurement of left ventricular pressures and dP/dt, a second catheter was implanted into the left ventricle through the right carotid artery. For measurement of cardiac output by a thermodilution method, a third catheter was implanted into the right atria through the right jugular vein for saline injection, and a thermistor catheter (Lyons Medical Instrument Co., Sylmar, Calif.) was inserted into the aortic arch.

The catheters were exteriorized at the back of the neck with the aid of a stainless steel wire tunneled subcutaneously and then fixed. Following catheter implantation, all rats were housed individually.

Hemodynamic measurements

One day after catheterization, hemodynamic measurements were made in the conscious and unrestrained rats. The thermistor catheter was processed using a microcomputer system (Lyons Medical Instrument Co.) for cardiac output determination, and the other three catheters were connected to a Model CP-10 pressure transducer (Century Technology Company, Inglewood, Calif., USA) coupled to a Grass Model 7 polygraph (Grass Instruments, Quincy, Mass., USA) for measurement of mean arterial pressure (MAP), systolic arterial pressure (SAP), heart rate (HR), left ventricular end-diastolic pressure (LVEDP) and left ventricular maximum dP/dt. For measurement of cardiac output, isotonic saline (0.1 mL) at room temperature was injected as a bolus via the jugular vein catheter. The thermodilution curve was monitored by VR-16 simultrace recorders (Honeywell Co., N.Y.) and cardiac output (CO) was digitally obtained by the microcomputer. From the CO the stroke volume (SV), cardiac index (CI), stroke volume index (SVI), and systemic vascular resistance (SVR) can be calculated.

After measurement of these hemodynamic parameters, 1 mL of blood was collected through the arterial catheter. Serum was separated and stored at −70° C. for measurement of GH and IGF-I.

At the conclusion of the experiments, rats were anesthetized with pentobarbital sodium (60 mg/kg) and the heart was arrested in diastole with intra-atrial injection of KCl (1M). The heart was removed, and the atria and great vessels were trimmed from the ventricle. The ventricle was weighed and fixed in 10% buffered formalin.

Infarct size measurements

The right ventricular free wall was dissected from the left ventricle. The left ventricle was cut in four transverse slices from apex to base. Five micrometer sections were cut, mounted and stained with Massons' trichrome stain. The endocardial and epicardial circumferences of the infarcted and non-infarcted left ventricle were determined with a planimeter Digital Image Analyzer. The infarcted circumference and the total left ventricular circumference of all four slices were summed and expressed as a percentage of infarcted circumference to total circumference. These two ratios were then averaged and expressed as a percentage for infarct size.

Hormone assays

Serum human GH was measured by a sensitive ELISA. Celniker, A., J. Clin. Endocrinol. Metab. 68:469–476 (1989); Greenen, D. L. et al., J. Appl. Physiol. 63:92–96 (1987). This assay does not detect rat GH. Total serum IGF-I was measured after acid-ethanol extraction by radioimmunoassay (Furlanetto R. W. et al., J. Clin. Invest. 60:648–657 [1977]; Zapf J. et al., J. Clin. Invest. 68:1321–1330, [1981]), using human IGF-I (available from Genentech, Inc. as a research reagent) as the standard and a rabbit anti-IGF-I polyclonal antiserum. The acceptable range was 1.25–40 ng/mL, while the intra- and inter-assay variabilities were 5–9% and 6–15%, respectively.

Statistical analysis

Results are expressed as mean±SEM. Two-way and one-way analysis of variance (ANOVA) was performed to assess differences in parameters between groups. Significant differences were then subjected to post hoc analysis using the Newman-Keuls method. $P<0.05$ was considered significant.

Results

Figure 1B:
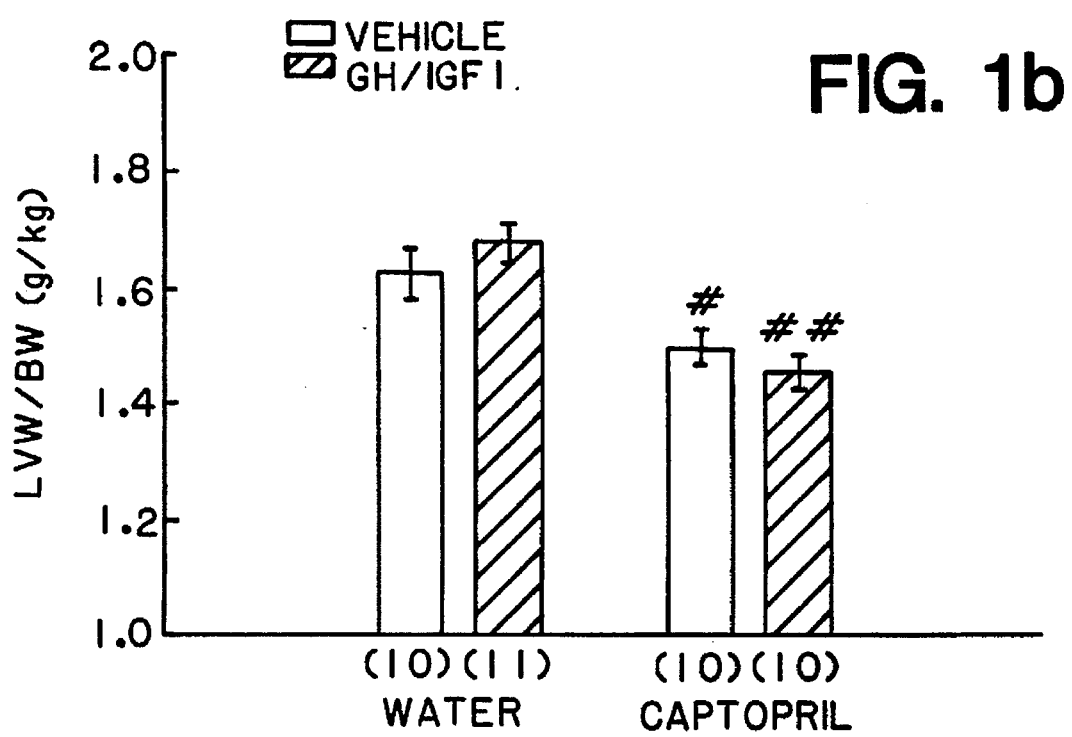
FIG. 1b shows the effect of GH/IGF-I (hatched bars) and vehicle alone (open bars) on the ratio of left ventricular weight to body weight (LVW/BW) in water-treated and captopril-treated rats. #$P<0.05$, ##$P<0.01$, compared to the respective water group.

The increase in BW was significantly greater in the GH/IGF-I-or captopril+GH/IGF-I-treated rats than in the captopril-treated or control rats. Captopril alone did not alter the BW increase. (FIG. 1a). GH/IGF-I did not significantly alter the ratio of left ventricular weight to BW (LVW/BW) in water-treated rats. The ratio of left ventricular weight to BW (LVW/BW) was significantly decreased in the captopril- or captopril+GH/IGF-I-treated group (FIG. 1b).

Figure 2A:
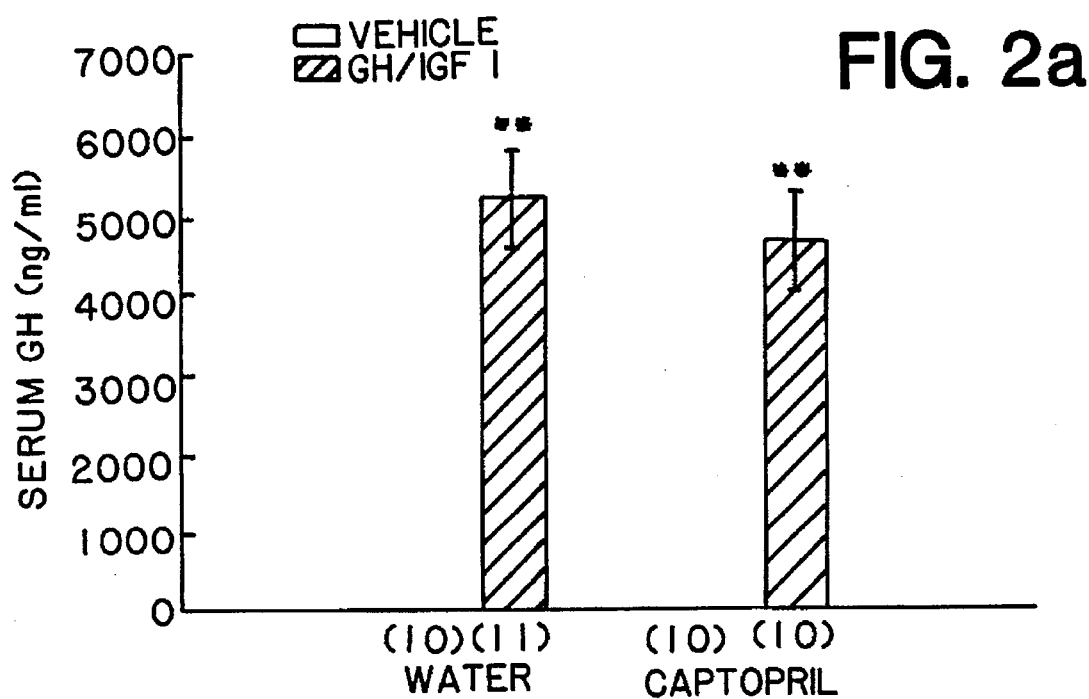
FIG. 2a shows the effect of GH/IGF-I (hatched bars) and vehicle alone (open bars) on serum levels of GH in water-treated and captopril-treated rats. **$P<0.01$, compared to the respective vehicle group.
Figure 2B:
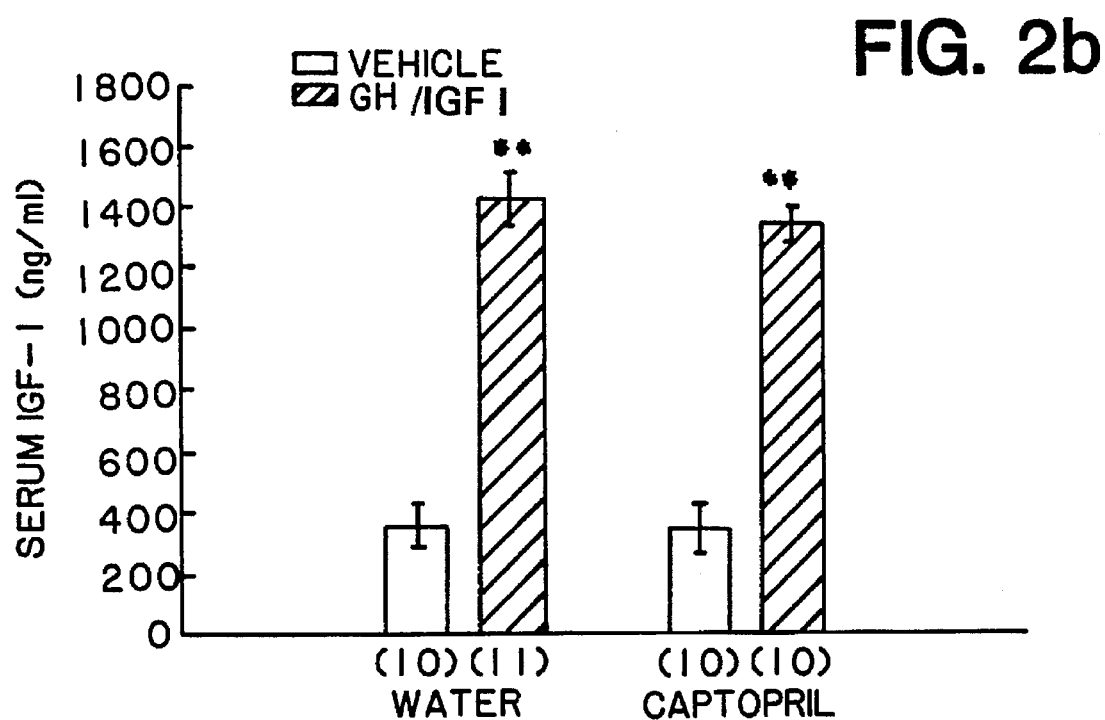
FIG. 2b shows the effect of GH/IGF-I (hatched bars) and vehicle alone (open bars) on serum levels of IGF-I in water-treated and captopril-treated rats. **$P<0.01$, compared to the respective vehicle group.

GH/IGF-I treatment significantly increased serum levels of human GH and human IGF-I in both water- and captopril-treated rats (FIG. 2a and FIG. 2b). The increase in serum levels of GH and IGF-I was not different between water- and captopril-treated rats.

Figure 3:
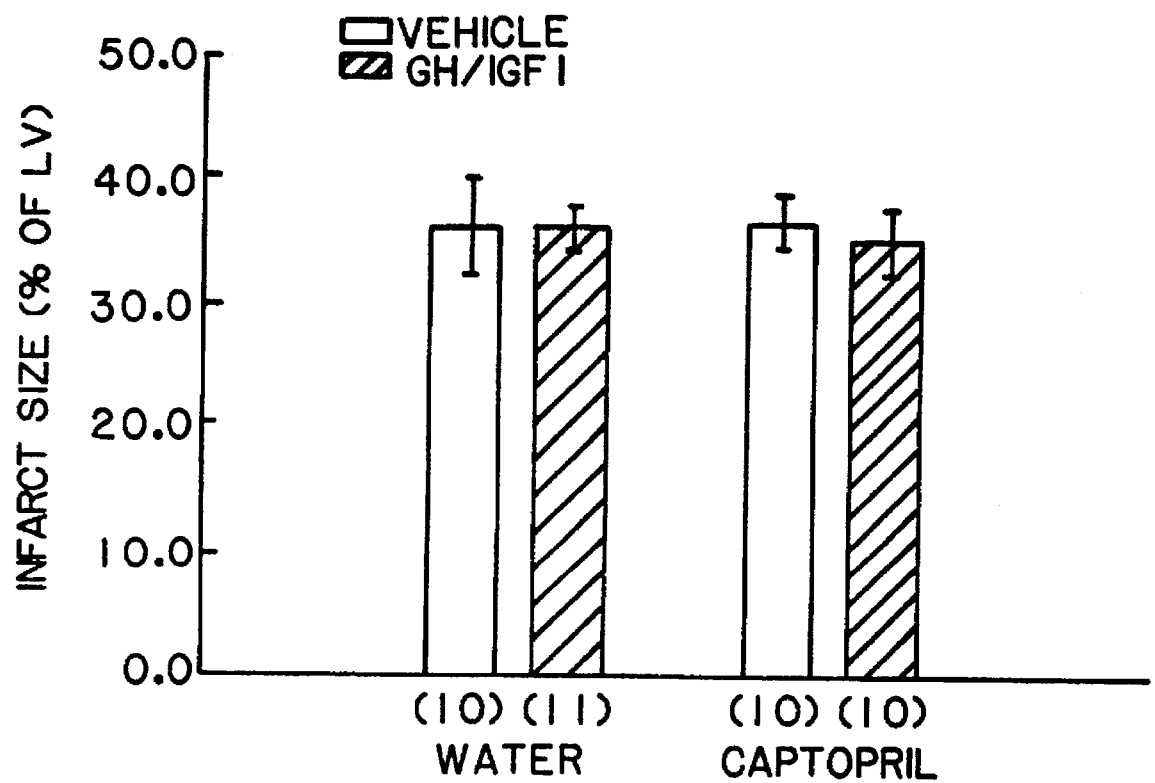
FIG. 3 shows the effect of GH/IGF-I (hatched bars) and vehicle alone (open bars) on infarct size in water-treated and captopril-treated rats.

Infarct size was not different in the four experimental groups (FIG. 3).

Figure 4A:
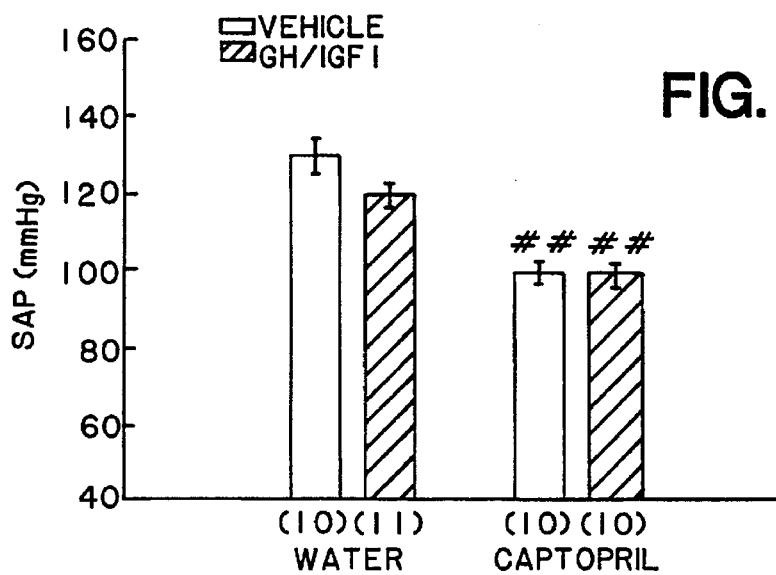
FIG. 4a shows the effect of GH/IGF-I (hatched bars) and vehicle alone (open bars) on systolic arterial pressure (SAP) in water-treated and captopril-treated rats. ##$P<0.01$, compared to the respective water group.
Figure 4B:
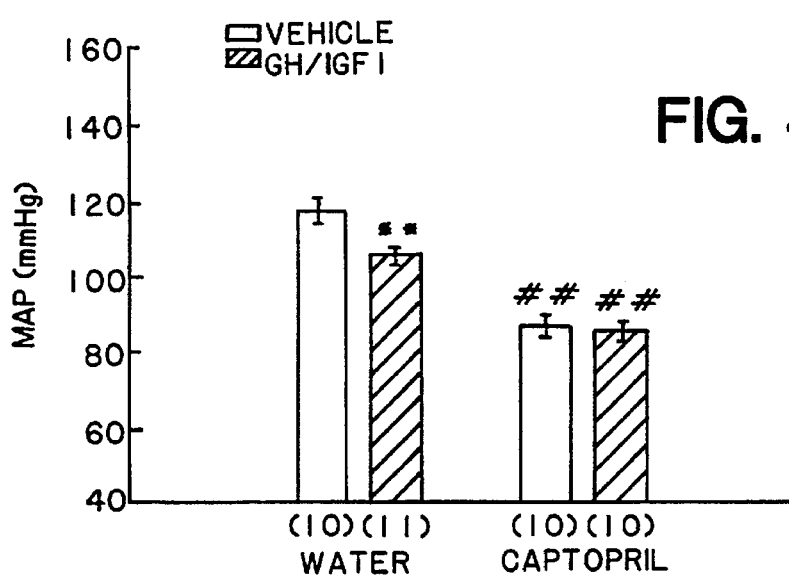
FIG. 4b shows the effect of GH/IGF-I (hatched bars) and vehicle alone (open bars) on mean arterial pressure (MAP) in water-treated and captopril-treated rats. **$P<0.01$, compared to the respective vehicle group. ##$P<0.01$, compared to the respective water group.
Figure 4C:
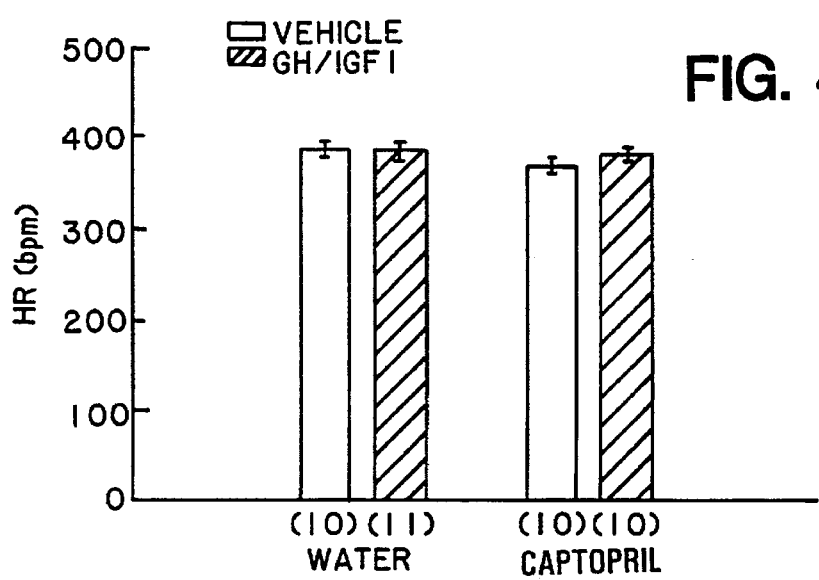
FIG. 4c shows the effect of GH/IGF-I (hatched bars) and vehicle alone (open bars) on heart rate (HR) in water-treated and captopril-treated rats.

GH/IGF-I tended to decrease SAP and significantly decrease MAP in water-treated rats (FIG. 4a and 4b). SAP and MAP were significantly reduced in the captopril- or captopril+GH/IGF-I-treated group compared to the control or GH/IGF-I group. Neither captopril nor GH/IGF-I altered HR significantly (FIG. 4c).

Figure 5A:
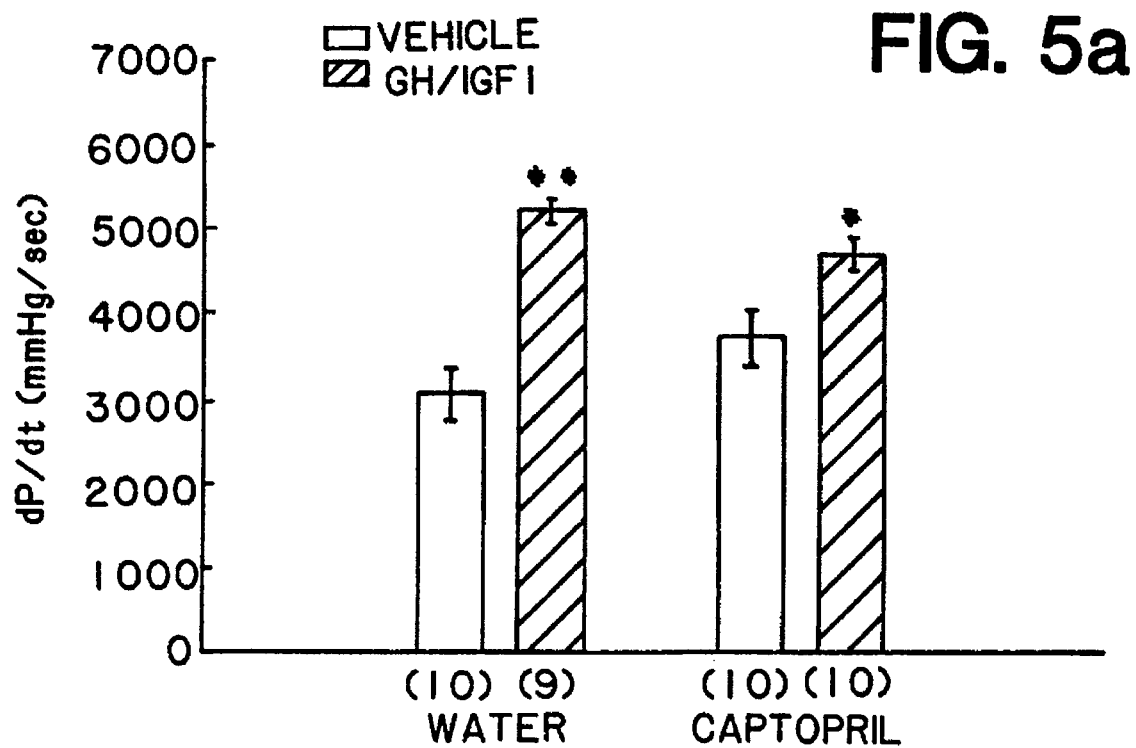
FIG. 5a shows the effect of GH/IGF-I (hatched bars) and vehicle alone (open bars) on left ventricular maximum dP/dt in water-treated and captopril-treated rats. *$P<0.05$, **$P<0.01$, compared to the respective vehicle group.
Figure 5B:
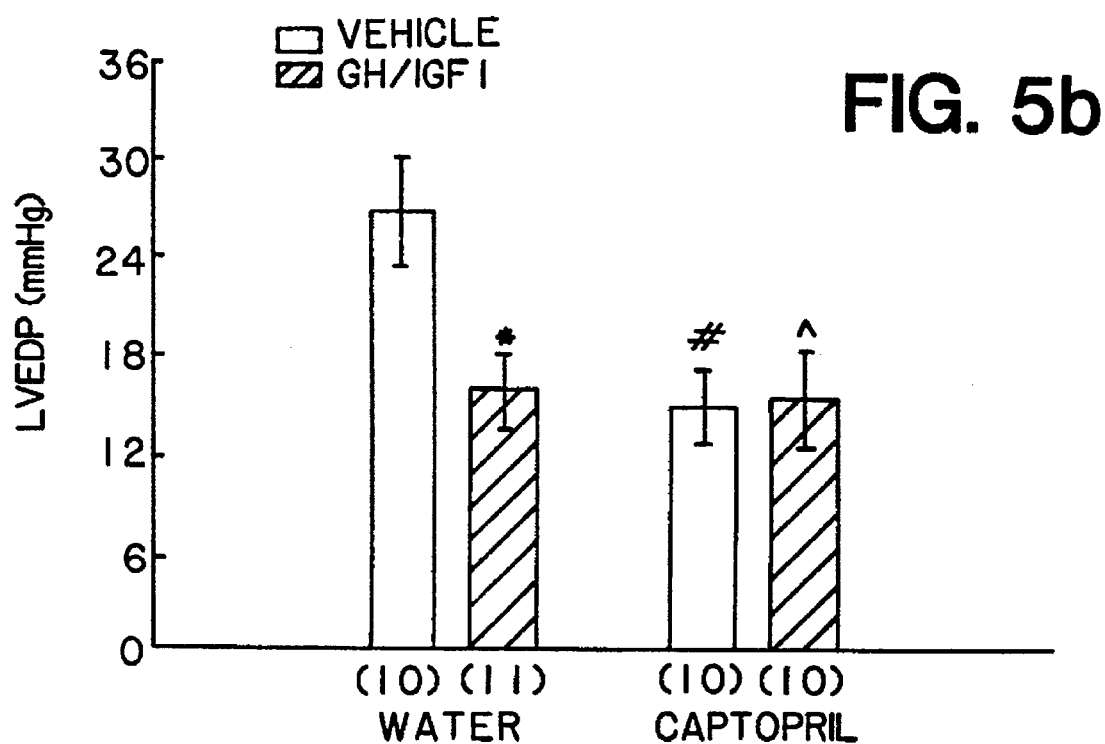
FIG. 5b shows the effect of GH/IGF-I (hatched bars) and vehicle alone (open bars) on left ventricular end-diastolic pressure (LVEDP) in water-treated and captopril-treated rats. *$P<0.05$, compared to the respective vehicle group. #$P<0.05$, compared to the respective water group. ^$P<0.01$, compared to the control (water+vehicle) group.

GH/IGF-I treatment caused a significant increase in left ventricular maximum dP/dt in both water- and captopril-treated rats (FIG. 5a). Captopril alone treatment did not alter dP/dt. LVEDP was significantly decreased in all three treated groups compared to the control group (FIG. 5b).

Figure 6A:
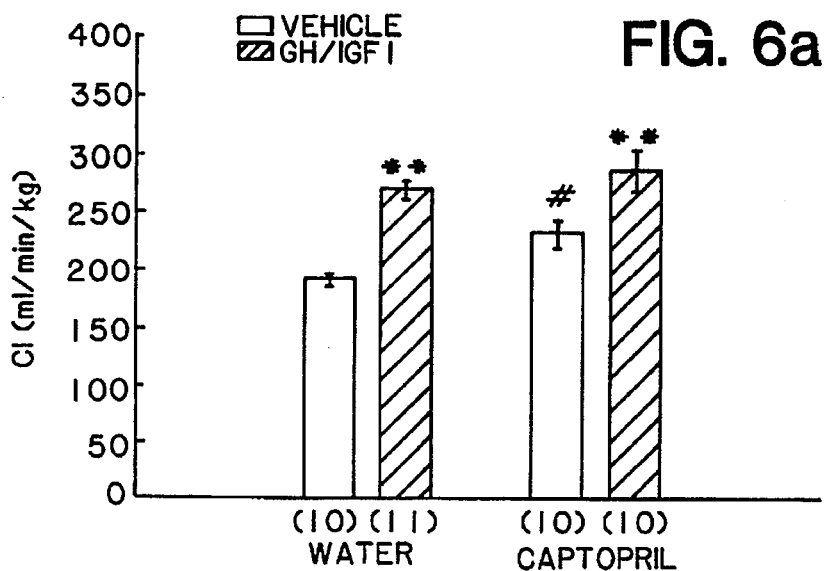
FIG. 6a shows the effect of GH/IGF-I (hatched bars) and vehicle alone (open bars) on cardiac index (CI) in water-treated and captopril-treated rats. **$P<0.01$, compared to the respective vehicle group. #$P<0.05$, compared to the respective water group.
Figure 6B:
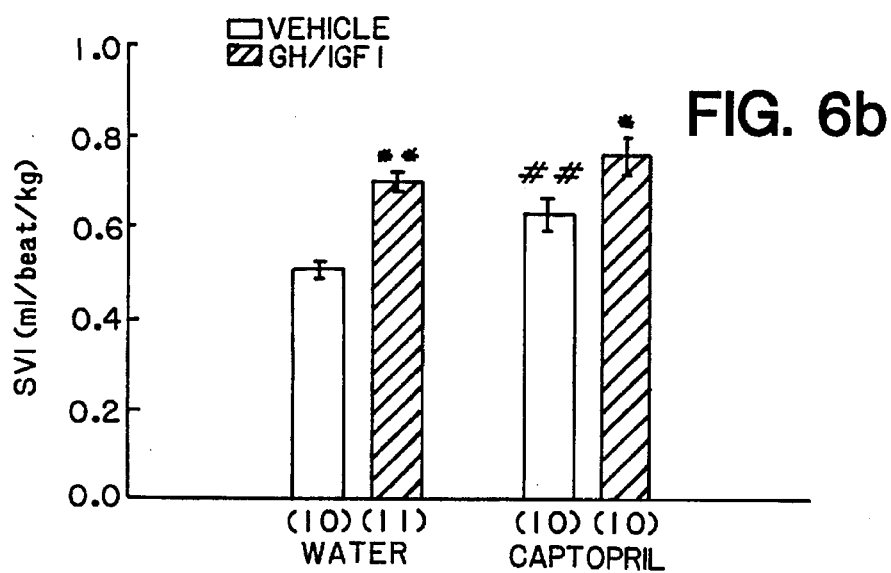
FIG. 6b shows the effect of GH/IGF-I (hatched bars) and vehicle alone (open bars) on stroke volume index (SVI) in water-treated and captopril-treated rats. *$P<0.05$, **$P<0.01$, compared to the respective vehicle group. ##$P<0.01$, compared to the respective water group.
Figure 6C:
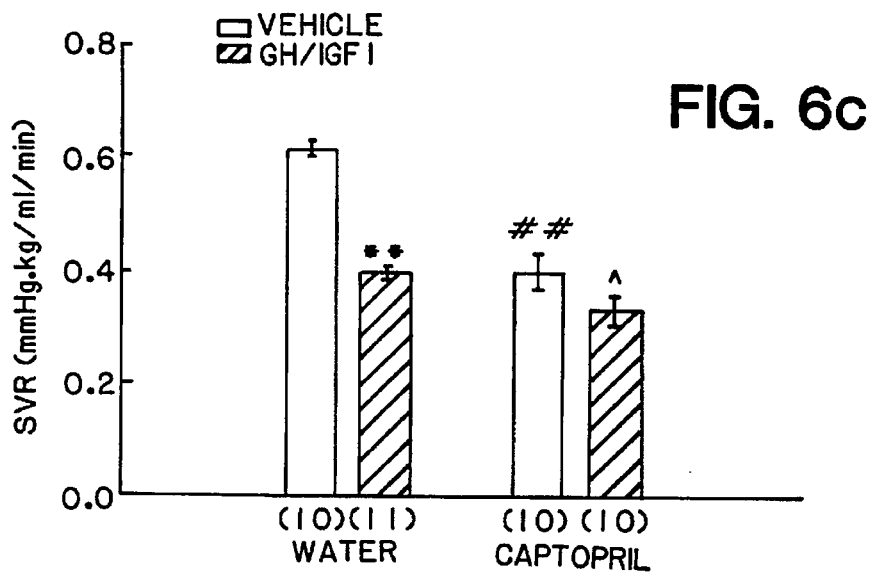
FIG. 6c shows the effect of GH/IGF-I (hatched bars) and vehicle alone (open bars) on systemic vascular resistance (SVR) in water-treated and captopril-treated rats. **$P<0.01$, compared to the respective vehicle group. ##$P<0.01$, compared to the respective water group. ^$P<0.01$, compared to the control (water+vehicle) group.

Either captopril or GH/IGF-I increased CI and SVI (FIG. 6a and 6b). The increase in CI and SVI was significantly greater in the captopril+GH/IGF-I-treated group than in the captopril-treated group. SVR was significantly reduced in the three treated groups compared to the control group (FIG. 6c).

Summary

Treatment for congestive heart failure with a combination of GH and IGF-I resulted in a significant increase in left ventricular maximum dP/dt, both in the presence and absence of captopril. This effect was not found with captopril alone.

Chronic treatment with captopril alone caused decreases in arterial pressure, left ventricular end-diastolic pressure and peripheral vascular resistance. These changes resulted in increased cardiac output and stroke volume in the test animals. These are the well known benefits of ACE inhibition which are manifest in humans and animals with heart failure.

GH and IGF-I added to the treatment regimen of a mammal with congestive heart failure after an initial period of treatment with captopril induced effects of increased myocardial contractility and cardiac performance which were apparent above the background of effect of chronic ACE inhibition. Furthermore, the beneficial effect of captopril in reducing cardiac hypertrophy, as measured by LVW/BW, is preserved in the group treated with captopril, GH, and IGF-I. The data suggest that captopril in combination with GH and IGF-I improves cardiac performance in congestive heart failure.

These results suggest that after a period of treatment with captopril or other ACE inhibitor, a patient with congestive heart failure will benefit from addition of GH and IGF-I to the treatment regimen. These results also suggest that a patient will benefit from a combination of GH and IGF-I, even in the absence of an ACE inhibitor. Patients benefitting from a combination of GH and IGF-I in the absence of an ACE inhibitor are those for whom an ACE inhibitor is contraindicated and those who cannot tolerate the side effects of an ACE inhibitor.

EXAMPLE 2

Proposed Clinical Treatment of Congestive Heart Failure

A. Intervention

Patient self-administration of GH and IGF-I in a single daily dose of GH and a twice daily dose of IGF-I is contemplated. The initial dose of each drug is expected to be administered on the same day, and would be 10 µg/kg/day of GH for groups 1, 2 and 3 and 40, 80, and 120 µg/kg/day of IGF-I (given twice daily) for groups 1, 2, and 3, respectively. After a week, the dose of GH would be kept constant at 10.0 µg/kg/day for group 1. For groups 2 and 3, the dose of GH would be increased to a final dose of 50 µg/kg/day and 100 µg/kg/day, respectively.

Dose would be adjusted downward for adverse effects (specifically, edema, symptomatic hypotension, salt retention refractory to increased diuretics, and fasting hyperglycemia>150 mg/do).

Concurrent medication doses (diuretics and ACE inhibitors) would be adjusted at the discretion of the study physician. For example, a test dose of captopril is optionally given to each of groups 1-3 at 6.25 mg and the dose is escalated as the patient tolerates it, up to a dose of 50 mg TID if successful. Alternatively, Vasotec® (enalapril) is given at a test dose at 5 mg and then is given at an escalated dose of 10-20 mg once a day.

The study would be stopped after four months of drug treatment; it is anticipated that in the event a beneficial effect is demonstrated, approximately half the patients would continue receiving the medication on a compassionate use basis. The remaining patients would undergo repeat assessment, including invasive hemodynamic monitoring, three months after discontinuation of drug treatment.

B. Inclusion Criteria

Patients would be considered for the study if they meet the following criteria:

Dilated cardiomyopathy (DCM). Idiopathic DCM, or ischemic DCM without discrete areas of akinesis/dyskinesis of the left ventricle (LV) on contrast ventriculography or 2D echocardiography. Evidence for impaired systolic function to include either LV end-diastolic dimension (EDD)>3.5 cm/m$^2$ BSA or EDV>90 mL/m$^2$ on 2D echocardiography, LV fractional shortening<25% on echocardiography, or ejection fraction (by contrast ventriculography or radionuclide angiography)<0.45.

Symptoms. New York Heart Association class III or peak exercise VO$_2 \leq$16 mL/kg/min. (adjusted for age), stable for at least one month on digoxin, diuretics, and ACE inhibitors (vasodilators).

Concurrent ACE inhibitor therapy, in absence of noncardiac contraindication.

Adequate echocardiographic "windows" to permit assessment of left ventricular volume and mass.

Ability to self-administer hGH and/or IGF-I according to the dosage schedule, and to reliably return for follow-up assessments.

Consent of patient and patient's primary physician to participate.

Absence of exclusion criteria.

In Phase 1, three patients would be enrolled in each of the three dosing groups (total of nine patients).

In Phase 2, fifteen patients would be enrolled in the open-label study (if echocardiographic and clinical parameters obtained during Phase 1 suggest an unexpectedly dramatic beneficial effect; fewer patients may be needed for Phase 2).

C. Exclusion Criteria

Patients would be excluded from consideration for any of the following reasons:

Heart failure resulting from uncorrected, primary valvular heart disease (operable or not), specific treatable etiologies (including alcohol, if abstinence has not been attempted), or operable coronary artery disease.

Dilated cardiomyopathy of less than three months duration.

Exercise limited by chest pain or obstructive peripheral vascular disease.

Chronic obstructive lung disease with FEV$_1 \leq$60% of predicted.

Diabetes mellitus or impaired glucose tolerance.

History of carpal tunnel syndrome, or evidence for positive Tinel's sign on examination.

Symptomatic osteoarthritis.

Inability to consent for or participate in serial bicycle ergometry with invasive hemodynamic monitoring (as described below).

Active malignancy.

D. Principal Measurements

1) Phase 1

Clinical: Symptoms, adverse effects.

Echocardiographic: LV mass, volume/mass ratio.

Laboratory: Glucose, BUN/creatinine, GH and IGF-I.

2) Phase 2

Clinical: NYHA Functional Class, Symptom Point Score (Kelly et al., *Am Heart J.* 119:1111 [1990]), BP, rales, jugular venous pressure (JVP), edema.

Echocardiographic: LV mass, LV dimensions and volume, volume/mass ratio, fractional shortening, ejection fraction, and end-systolic and end-diastolic wall stress.

Hemodynamic: VO$_{2max}$; cardiac index (CI), pulmonary capillary wedge pressure (PCW), and systemic vascular resistance (SVR) at rest and at maximal exercise.

Laboratory: Serum sodium, Bun/creatinine, neurohormonal status (norepinephrine), atrial natriuretic peptide (ANP), plasma renin activity (PRA).

E. Patient Assessment

Run-in period. Assessment would include baseline determination of functional status, UCSD Symptom Point Score, physical examination (described below), baseline echocardiography (described below), laboratory data (described below), and noninvasive measurement of VO$_{2max}$ by bicycle ergometry.

Pretreatment assessment. It is anticipated that patients would remain in the hospital for two to three days at the onset of treatment. Assessment would include determination of functional status, UCSD Symptom Point Score, physical examination (described below), baseline echocardiography (described below), laboratory data (described below), rest/exercise hemodynamics (described below), and a Six Minute Walk test.

Daily in-hospital assessment would include symptom status, body weight, survey for symptoms of adverse drug reactions, and fasting glucose. After discharge, patients would be contacted by telephone every 3 days for the first 2 weeks to detect adverse drug reactions or worsening clinical status.

Weekly visits would consist of body weight, physical examination, and functional status. Laboratory data, including fasting glucose, electrolytes, BUN and creatinine, and liver function tests, would be performed weekly for the first four weeks, then once after the second month. Every 4 weeks, echocardiography would be performed. Increasing dyspnea or peripheral edema would be treated with an increase in diuretic dose; hypotension would be treated by reduction in vasodilator dose.

After 4 months the studies described under "Pretreatment assessment" would be repeated.

Three months after drug discontinuation, the studies described under "Pretreatment assessment" would again be repeated.

i. Physical examination for JVP, rales, and peripheral edema.

ii. UCSD Symptom Point Score.

iii. Laboratory data: Electrolytes (including $Ca^{2+}$, $Mg^{2+}$, and phosphorus), BUN, and creatinine; fasting glucose and lipid profile (total cholesterol, HDL-C, LDL-C, triglycerides); liver function tests (AST, ALT, alkaline phosphatase, total bilirubin), uric acid, fasting lipid profile (total cholesterol, HDL-C, LDL-C, triglycerides); GH and IGF-I levels; plasma NE, ANP, PRA.

iv. Echocardiography: diastolic and systolic dimensions at the papillary muscle level; ejection fraction estimate by area planimetry from apical 2 chamber and 4 chamber views, fractional shortening, estimated systolic and diastolic volumes by Simpson's rule method, fractional shortening, and estimated left ventricular mass; doppler assessment of mitral valve inflow profile (IVRT, peak E, peak A, deceleration time, A wave duration) and pulmonary vein flow profile (systolic flow area, diastolic flow area, A reversal duration and velocity). Calculated values would include volume/mass ratio and end-systolic and end-diastolic wall stresses.

v. Rest and exercise hemodynamics and measured oxygen consumption, using bicycle ergometry with percutaneously inserted pulmonary artery and arterial catheters. Perceived exertion level would be scored on the Borg scale, and measurements of pulmonary artery systolic, diastolic, and mean pressures, as well as arterial pressures and pulmonary capillary wedge pressure would be taken at each increment of workload, along with arterial and mixed venous oxygen content for calculating cardiac output, using measured $O_2$ consumption. Calculated values would include SVR and pulmonary vascular resistance.

vi. Six Minute Walk. As described by Bittner et al. (*JAMA*, 270:1702–1707 [1993]), the distance covered by the patient along a 100 foot course, walking at their own maximum pace, in six minutes.

a) Major Assessment Points

Major assessment points would occur at baseline (prior to initiation of active treatment), after peak stable drug dose maintained for the time period determined in Phase 1 (anticipated to be 12–16 weeks), and after an equal period of time after drug discontinuation.

i. Physical examination.

ii. Symptom Point Score.

iii. Laboratory data: Electrolytes, BUN, and creatinine; fasting glucose and lipid profile (total cholesterol, HDL-C, LDL-C, triglycerides); growth hormone, IGF-I; plasma NE, ANP, PRA.

iv. Echocardiography: diastolic and systolic dimensions at the papillary muscle level; ejection fraction estimate by area planimetry from apical 2 chamber and 4 chamber views, fractional shortening, estimated systolic and diastolic volumes by Simpson's rule method, fractional shortening, and estimated left ventricular mass; Doppler assessment of mitral valve inflow profile (IVRT, peak E, peak A, deceleration time, A wave duration) and pulmonary vein flow profile (systolic flow area, diastolic flow area, A reversal duration and velocity). Calculated values would include volume/mass ratio and end-systolic and end-diastolic wall stresses.

v. Rest and exercise hemodynamics and measured oxygen consumption, using bicycle ergometry with percutaneously inserted pulmonary artery and arterial catheters. Perceived exertion level would be scored on the Borg scale, and measurements of pulmonary artery systolic, diastolic, and mean pressures, as well as arterial pressures and pulmonary capillary wedge pressure would be taken at each increment of workload, along with arterial and mixed venous oxygen content for calculating cardiac output, using measured oxygen consumption. Calculated values would include SVR and pulmonary vascular resistance.

b) Interim assessment points: weekly i. Physical examination.

ii. Symptom Point Score.

F. Potential Benefits

1) Improved sense of well-being.
2) Increased exercise tolerance.
3) Increased muscle strength and lean body mass.
4) Decreased systemic vascular resistance.
5) Enhanced cardiac performance.
6) Enhanced compensatory myocardial hypertrophy.

What is claimed is:

1. A method of treating congestive heart failure in a mammal who is not a GH-deficient adult, said method comprising administering to said mammal an effective amount of a combination of GH and IGF-I.

2. The method of claim 1 wherein the growth hormone is human growth hormone and the IGF-I is human IGF-I.

3. The method of claim 2 wherein the mammal is a human.

4. The method of claim 3 wherein the effective amount of each of GH and IGF-I is between about 0.01 and about 1 mg/kg/day.

5. The method of claim 4 wherein the administration of GH or IGF-I or both is by the subcutaneous or intravenous route.

6. The method of claim 5 wherein the GH is administered once daily and the IGF-I is administered twice daily.

7. The method of claim 1 wherein the congestive heart failure results from acute or chronic ischemia.

8. The method of claim 1 wherein the congestive heart failure results from myocardial infarction.

* * * * *